US010068337B2

(12) United States Patent
Wang

(10) Patent No.: US 10,068,337 B2
(45) Date of Patent: Sep. 4, 2018

(54) DEVICE AND METHOD FOR DIAGNOSING THERMAL IMAGES

(71) Applicant: Mission Infrared Electro Optics Technology Co., Ltd, Hangzhou, Zhejiang (CN)

(72) Inventor: Hao Wang, Hangzhou (CN)

(73) Assignee: MISSION INFRARED ELECTRO OPTICS TECHNOLOGY CO., LTD, Hangzhou (CN)

( * ) Notice: Subject to any disclaimer, the term of this patent is extended or adjusted under 35 U.S.C. 154(b) by 305 days.

(21) Appl. No.: 14/430,212

(22) PCT Filed: Sep. 22, 2013

(86) PCT No.: PCT/CN2013/083955
§ 371 (c)(1),
(2) Date: Mar. 21, 2015

(87) PCT Pub. No.: WO2014/044221
PCT Pub. Date: Mar. 27, 2014

(65) Prior Publication Data
US 2015/0254860 A1    Sep. 10, 2015

(30) Foreign Application Priority Data

Sep. 21, 2012 (CN) .......................... 2012 1 0356230

(51) Int. Cl.
*G06T 1/00* (2006.01)
*G06T 7/00* (2017.01)
(Continued)

(52) U.S. Cl.
CPC ............ *G06T 7/0046* (2013.01); *A61B 5/015* (2013.01); *G01J 5/025* (2013.01); *G01J 5/089* (2013.01);
(Continued)

(58) Field of Classification Search
CPC ........ A61B 5/015; G01J 5/025; G01J 5/0859; G01J 5/089; G01J 2005/0077;
(Continued)

(56) References Cited

U.S. PATENT DOCUMENTS

2008/0075321 A1* 3/2008 Kabasawa ............... G01R 33/54
382/100
2013/0314221 A1* 11/2013 Taylor .................... G06T 7/174
340/435

FOREIGN PATENT DOCUMENTS

| CN | 102538974 A | 7/2012 |
| CN | 102538980 A | 7/2012 |
| CN | 102564607 A | 7/2012 |

OTHER PUBLICATIONS

English machine translation of Wang (CN 102564607), Accessed Mar. 16, 2017.*

(Continued)

*Primary Examiner* — Edward Park

(57) ABSTRACT

This invention provides a device and method for diagnosing thermal images, which relates to a thermal imaging device and an applied field of infrared detection. The conventional thermal imaging device is excessively dependent on subjective experience of users to set an analysis area and mode of a thermal image during photographing, causing complicated operation and affecting assessments of thermal images. In the invention, a reference image reflecting morphological characters of a photographed body is superimposed and displayed in an infrared thermal image, and is as a visual reference of the photographed thermal image. The thermal image is diagnosed according to a corresponding analysis area and a specified diagnosis mode, to acquire a diagnosis result. Thereby, the common users can achieve the better photographing level.

24 Claims, 17 Drawing Sheets

(51) Int. Cl.
*A61B 5/01* (2006.01)
*G01J 5/08* (2006.01)
*G01J 5/02* (2006.01)
*G06K 9/62* (2006.01)
*G06K 9/03* (2006.01)
*G06K 9/20* (2006.01)
*G06T 7/73* (2017.01)
*G01J 5/00* (2006.01)

(52) U.S. Cl.
CPC ............ *G01J 5/0859* (2013.01); *G06K 9/033* (2013.01); *G06K 9/2018* (2013.01); *G06K 9/6227* (2013.01); *G06T 7/74* (2017.01); *G01J 2005/0077* (2013.01); *G06K 2209/19* (2013.01); *G06T 2207/10048* (2013.01); *G06T 2207/30164* (2013.01)

(58) Field of Classification Search
CPC .... G06K 9/033; G06K 9/2018; G06K 9/6227; G06K 2209/19; G06T 7/0046; G06T 7/74; G06T 2207/10048; G06T 2207/30164
See application file for complete search history.

(56) References Cited

OTHER PUBLICATIONS

International Search Report of PCT Patent Application No. PCT/CN2013/083955 dated Jan. 16, 2014.

* cited by examiner

| body information | reference image |
|---|---|
| photographed body 1 | constituted data of T1 |
| photographed body 2 | constituted data of T2 |
| photographed body 3 | constituted data of T2 |
| ... | ... |

FIG. 3

| body information | benchmark 1 | benchmark 2 | auxiliary 1 | analysis mode 1 | analysis mode 2 | diagnosis rule 1 | diagnosis rule 2 |
|---|---|---|---|---|---|---|---|
| photographed body 1 | constituted data of T1 | constituted data of TU1 | constituted data of F1 | mode information of F1 | information of mode 2 | diagnosis rule of F1 | diagnosis rule to which the mode 2 corresponds |
| photographed body 2 | constituted data of T2 | constituted data of TU2 | constituted data of F2 | mode information of F2 | | diagnosis rule of F2 | |
| photographed body 3 | constituted data of T3 | constituted data of TU3 | constituted data of F3 | mode information of F3 | | diagnosis rule of F3 | |
| ... | ... | ... | ... | ... | ... | ... | ... |

| constituted data | processing object | processing algorithm | | | |
|---|---|---|---|---|---|
| | | cutting | range extracting | contour extracting | ... |
| benchmark 1 | ● | ● | | | |
| benchmark 2 | | | | | |
| auxiliary 1 | | | | | | object processing — CD11, CD12, CD13

FIG. 11

| constituted data | computing object | algorithm and parameter | | | | | |
|---|---|---|---|---|---|---|---|
| | | scaling | deforming | center line | bounding rectangle | feature point | ... |
| benchmark 1 | ● | | | | ● | | |
| benchmark 2 | | | | | | | |
| auxiliary 1 | | | | | | | |
| benchmark 1 (processing) | | | | | | | | object computing — CD21, CD22, CD23

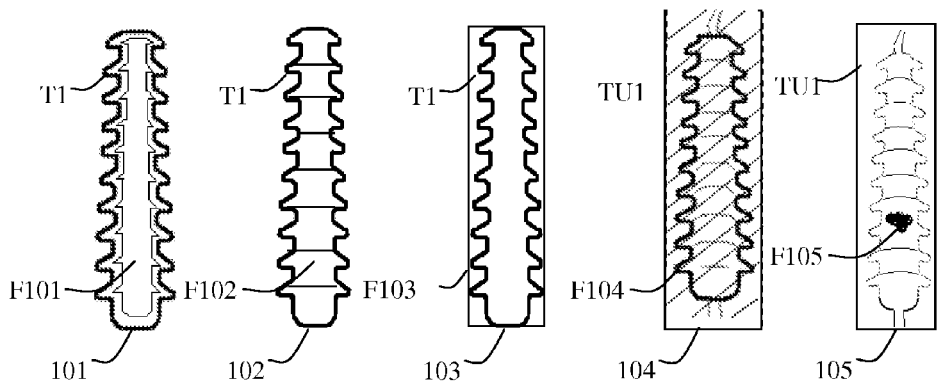

FIG. 12

| constituted data | reference image | position rule | | | | synthesis parameter | | | | analysis area | analysis mode and diagnosis rule | | | diagnosis configuration |
|---|---|---|---|---|---|---|---|---|---|---|---|---|---|---|
| | | main object | self-adaption | designated position | relevance | synthesis sequence | transparency ratio | color | relevance | | analysis diagnosis 1 | analysis diagnosis 2 | others | |
| | | CD33 | | | | CD34 | | | | CD35 | CD36 | | | |
| CD31 | CD32 | | | | | | | | | | | | | |
| benchmark 1 | ● | | | | | 1 | 1 | | | | | | | |
| benchmark 2 | | | | | | | | | | | | | | |
| auxiliary 1 | ● | ● | ● | | | 2 | 1 | | | ● | ● | | | |
| benchmark 1 (computing) | | | | | | | | | | | | | | |
| benchmark 1 (processing) | | | | | | | | | | | | | | |

FIG. 13

| constituted data | reference image | position rule | | | | synthesis parameter | | | | analysis area | analysis mode and diagnosis rule | | | switch configuration |
|---|---|---|---|---|---|---|---|---|---|---|---|---|---|---|
| | | main object | self-adaption | designated position | relevance | synthesis sequence | transparency ratio | color | relevance | | analysis diagnosis 1 | analysis diagnosis 2 | others | |
| | | CD33 | | | | CD34 | | | | CD35 | CD36 | | | |
| CD31 | CD32 | | | | | | | | | | | | | |
| benchmark 1 | ● | | | | | 1 | 1 | | | | | | | |
| benchmark 2 | | | | | | | | | | | | | | |
| auxiliary 1 | ● | ● | ● | | | 2 | 1 | | | ● | ● | | | |
| benchmark 1 (computing) | | | | | | | | | | | | | | |
| benchmark 1 (processing) | | | | | | | | | | | | | | |

FIG. 14

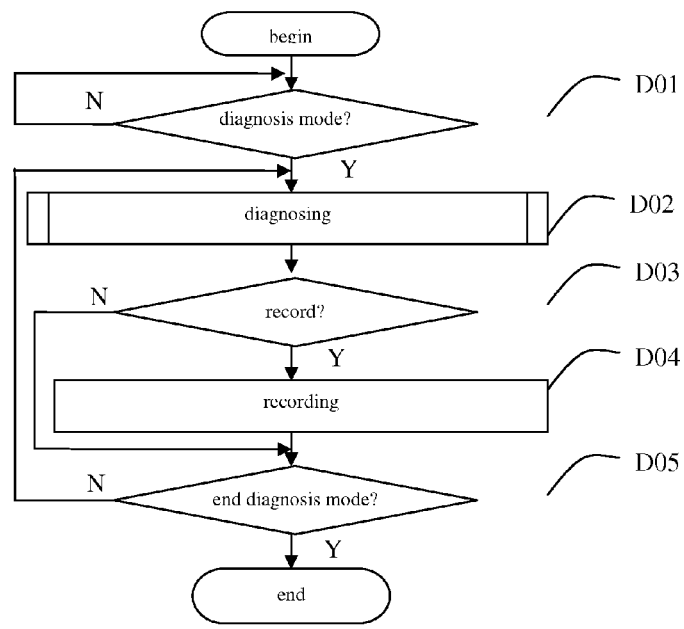
FIG. 30
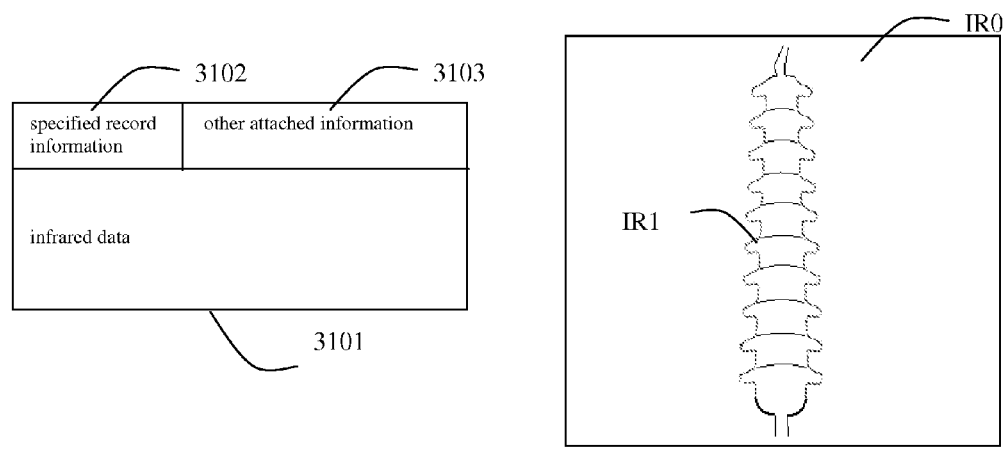
FIG. 31
FIG. 32

DEVICE AND METHOD FOR DIAGNOSING THERMAL IMAGES

BACKGROUND OF THE INVENTION

Field of the Invention

This invention relates to a thermal imaging device, a thermal image processing device, and infrared detection field and, more particularly, to a device and a method for diagnosing thermal images.

Description of the Related Art

A thermal imaging device generates images by receiving infrared radiation of a photographed body. At present, a user is necessary to depend on subjective experience to manually set an analysis area of a specified part of a body thermal image, to acquire an analysis result of the thermal image, and the user may diagnose the state of the photographed body by observing the thermal image of the photographed body and the analysis result. The analysis area corresponds to the specified part in an infrared thermal image to be analyzed, such as area units, i.e. points, lines, or planes, or a combination of the multiple area units.

First, even if the analysis area is set, the use is still inconvenient. As the user fails to directly understand the position in the body thermal image where the analysis area should be according to an analysis area F1 in FIG. 6, when the next photographed body of the same type is photographed, the preset analysis area fails to correspond to a correct part of the body thermal image (such as, different sizes of the body thermal images or different positions of the body thermal images in an infrared thermal image), thereby causing the analysis result with great discrete and being difficult to perform effective diagnosis.

Second, the setting operation of the analysis area is complicated and may cause a mistake. For example, as numbers, types, positions, or sizes of area units S01, S02 of the analysis area F1 in FIG. 6 change, the final analysis result may be different. The manual setting operation (such as selecting the type of the analysis area, such as points, lines, or planes, and disposing at a corresponding position of the body thermal image) is very complicated. The analysis area may be set, depending on the understanding of the user for an analysis part of a photographed body. Different photographed bodies have the respective analysis part, which requires great skill. Due to the above reasons, it is inconvenient to perform the setting of the complicated analysis area.

Further, the operation of setting the analysis mode corresponding to the analysis area is also complicated. The different settings of the analysis mode acquire different analysis results. The analysis mode is set, depending on the understanding of the user for the analysis parts, analysis methods, and diagnosing method of different photographed bodies, which requires great skill. The analysis mode represents an analysis computing rule used by acquiring the analysis result after specified analysis for the thermal imaging data determined by the analysis area, such as computing the maximum temperature, average temperature, minimum temperature, or a percentage content, and a computing relation between different area units, i.e. difference in temperature.

The operation of setting the analysis area, the analysis mode, and the diagnosis rule by users needs high technical requirements. With regard to the thermal images of a photographed body, the part that the analysis area corresponds to, the applied analysis mode, and the diagnosis rule have strict requirements. Therefore, the users need to be professional in analysis of the thermal images of the photographed body. For example, in power industry, according to the power industry specification, different photographed bodies, such as a switch, a lightning protector, a cable terminating set, have special analysis parts, special analysis modes, and diagnosis rules. Taking the cable terminating set for example, the analysis area may be set at specified parts of an upper portion and a lower portion of a main body sleeve, and then the respective maximum temperature and the temperature difference therebetween may be calculated. If the analysis area is not accurately set at the above parts, or the analysis mode is unreasonable, the correct analysis data fails to be acquired. The users need to master the diagnosis basis of the photographed body, further to set the diagnosis rule, which needs high requirements. However, there are dozens of the types of the photographed body that needs infrared detection in the power industry. According to the different voltage classes, there may be thousands of the types, and the technical difficulty is obvious.

Due to the above reasons, at present, the users perform simple analysis based on experience, such as setting automatically capture of the maximum temperature at most conditions. However, the extensive way may reduce the reference value of the analysis result during photographing. Further, since the analysis data acquired above has great discreteness, the smart diagnosis for the photographed body during photographing is very difficult, and the breakdown may be omitted.

Therefore, a thermal imaging device capable of allowing the set analysis area to conveniently photograph the next photographed body of the same type, ensuring the photographing quality, and having the analysis and diagnosis function is needed. Thus, the diagnosis according to the analysis result is useful.

Further, the analysis area of the body thermal image to be specially analyzed may be set conveniently, and further the analysis mode corresponding to the analysis area may be set easily, thus to acquire the reliable analysis result. Further, the setting of the diagnosis rule is necessary to depend on the understanding of the users for the analysis and diagnosis of different body thermal images, which requires greater skill. If the setting of the diagnosis rule to which the analysis mode corresponds may be solved, the accurate diagnosis result may be conveniently acquired. Thereby, the common user can achieve the better infrared photographing level.

BRIEF SUMMARY OF THE INVENTION

As for the deficiencies of the prior art, this invention provides a device and a method for diagnosing thermal images. In an infrared thermal image, a reference image reflecting predetermined morphological characters of a photographed body is displayed, the reference image is used as a visual reference for photographing a thermal image, the thermal image of the photographed body is analyzed according to an analysis area and an analysis mode, and an analysis result is diagnosed according to a specified diagnosis rule to acquire a diagnosis result. Thereby, the diagnosis may be useful, and the common users can achieve the better photographing level.

This invention provides a device for diagnosing thermal images including the followings.

An acquiring part is used for acquiring thermal imaging data. A reference image designating part is used for designating constituted data for acquiring a reference image reflecting morphological characters of a photographed body. An analysis area determining part is used for determining the constituted data of an analysis area. The reference image position setting part is used for setting a position parameter of the reference image in an infrared thermal image. An analysis area position setting part is used for setting the position parameter of the analysis area in the infrared thermal image. A display controlling part is used for controlling to display the reference image acquired according to the designated constituted data and the infrared thermal image generated by the acquired thermal imaging data together according to the position parameter of the reference image. A thermal image analyzing part is used for analyzing the thermal imaging data acquired by the acquiring part or the data acquired after the specified processing to acquire an analysis result according to a specified analysis mode, based on the analysis area with the position parameter. A diagnosing part is used for diagnosing according to a specified diagnosis rule to acquire a diagnosis result according to the analysis result acquired by the thermal image analyzing part. The reference of the reference image may assist the users to photograph the thermal image of the photographed body with the high quality, and after the analysis area is set, the next photographed body of the same type may be photographed conveniently, thereby ensuring the correction and consistency of the analysis and diagnosis. Thus, the diagnosis performed after setting the diagnosis rule is useful.

Further, the analysis mode at least includes one or a combination of the followings:

1) the analysis mode acquired according to analysis mode information related to the constituted data of the determined analysis area;

2) the analysis mode acquired according to the analysis mode information related to a position rule or position information related to the position parameter of the acquired analysis area;

3) the analysis mode acquired according to the analysis mode information related to a corresponding computing and/or processing rule and/or the analysis mode information related to a designated object, when the constituted data of the analysis area is acquired by computing and/or processing the designated object.

Thereby, the analysis mode may be set automatically or conveniently according to the set constituted data, thereby facilitating complicated analysis.

Further, the diagnosis rule at least includes the diagnosis rule set according to the diagnosis rule related to the analysis mode. Thereby, the diagnosis may be performed according to the analysis mode and the related diagnosis rule, thereby facilitating complicated diagnosis and avoiding setting the diagnosis rule.

Further, a body information selecting part is used for selecting body information from a storage medium. The storage medium is used for storing at least one body information and the constituted data related to the body information. The reference image designating part is used for designating the constituted data for acquiring the reference image according to the constituted data related to the selected body information. The analysis area determining part is used for determining the constituted data of the analysis area according to the constituted data related to the selected body information. Thus, the correction and convenience of the selected reference image and the analysis area may be ensured. The users may select according to the cognitive body information on the scene, thereby avoiding confusion caused by incorrect selection of the constituted data.

Further, the reference image designating part and the analysis area determining part are used for determining the constituted data of the reference image and the constituted data of the analysis area according to a specified designated type of the constitute data, thereby achieving the simple operation.

Further, the constituted data of the reference image and the constituted data of the analysis area have a specified position relation, and the displayed reference image and the analysis area related to analysis satisfy the specified position relation. Thus, the set reference image and the analysis area are standard and correct, thereby facilitating to subsequently acquire the accurate analysis result and the diagnosis result.

Further, the reference image designating part and the analysis area determining part are used for determining the constituted data of the reference image and the constituted data of the analysis area according to the related constitute data, thereby simplifying the operation of the users.

Further, the storage medium is used for storing at least one body information and the constituted data with the specified position relation related with the body information. The body information selecting part is used for selecting the body information. The reference image designating part and the analysis area determining part are used for determining the constituted data of the reference image and the constituted data of the analysis area according to the constituted data with the specified position relation related to the selected body information.

Further, the constituted data of the analysis area at least includes the constituted data of the analysis area acquired by processing a designated object according to a specified processing rule and/or computing the designated object according to a specified computing rule. Thus, the accurate analysis area may be ensured, the accuracy of the subsequent analysis and diagnosis may be ensured, and the operation is automatic and simple.

Further, the analysis area is the analysis area set according to the specified position having the specified position relation with the reference image. Thus, the analysis area may be accurate and may be adjusted conveniently, thereby ensuring the accuracy of the subsequent analysis and diagnosis, and achieving automatic and simple operation.

Further, the reference image position setting part and the analysis area position setting part are used for setting position parameters of the reference image and the analysis area in the infrared thermal image according to a specified position rule, thereby achieving the simple operation via automatic settings.

Further, the storage medium is used for storing the constituted data and the related position information. The position information represents the position information of the reference image and/or the analysis area acquired by the constituted data in the infrared thermal image. The reference image position setting part and the analysis area position setting part are used for setting the position parameter of the reference image and/or the analysis area in the infrared thermal image according to the position information related to the constituted data of the designated reference image and the position information related to the constituted data of the analysis area. Thus, the operation is simple via automatic settings.

Further, the reference image position setting part and the analysis area position setting part are used for setting the position parameters of the reference image and the analysis area according to one of the followings: 1) the position parameter of the reference image is first set, and then the position parameter of the analysis area is set according to the specified position relation between the reference image and the analysis area; 2) the position parameter of the analysis area is set first, and then the position parameter of the reference image is set according to the specified position relation between the reference image and the analysis area; 3) the position parameter of the reference image and/or the analysis area is set according to the position parameter of a main object and the specified position relation between the reference image and/or the analysis area and the main object. Thus, the operation is simple, and the analysis is flexible.

Further, the storage medium is used for storing at least one body information, the constituted data related to the body information, the analysis mode information related to the constituted data, and diagnosis rule information related to the analysis mode information. The thermal image analyzing part is used for analyzing the thermal imaging data acquired by the acquiring part or the data acquired after specified processing to acquire an analysis result according to the specified analysis mode based on the analysis area with the position parameter. The analysis mode at least includes the analysis mode acquired by the analysis mode information related to the constituted data of the acquired analysis area. The diagnosing part is used for diagnosing according to the specified diagnosis rule to acquire a diagnosis result according to the analysis result acquired by the thermal image analyzing part. The diagnosis rule at least includes the diagnosis rule acquired according by the diagnosis rule information related to the analysis mode information. After the body information is selected, the above determination processing may be performed via automatic or simple operation, thereby facilitating to select the correct reference image, the analysis area, the analysis mode, and the diagnosis rule, and achieving the simple operation.

Further, a configuration part is used for configuring a specified designated type of the constituted data of the reference image, a specified designated type of the constituted data of the analysis area, a position setting rule of the reference image and the analysis area, an analysis mode to which the analysis area corresponds, the diagnosis rule to which the analysis mode corresponds, or a combination thereof. Thus, the users may conveniently configure the reference image, the analysis area, the analysis mode, or the diagnosis rule, thereby achieving the subsequent repeated use.

Further, a record part is used for recording specified record information with the acquired thermal imaging data or the data acquired after specified processing for the acquired thermal imaging data, thereby facilitating the subsequent batch processing. When the acquired diagnosis result is record, the speed of the batch processing may be accelerated.

This invention provides a method for diagnosing thermal images including the following steps.

An acquiring step is used for acquiring thermal imaging data.

A reference image designating step is used for designating constituted data for acquiring a reference image reflecting morphological characters of a photographed body.

An analysis area determining step is used for determining the constituted data of the analysis area.

A reference image position setting step is used for setting the position parameter of the reference image in an infrared thermal image.

An analysis area position setting step is used for setting the position parameter of the analysis area in the infrared thermal image.

A display controlling step is used for controlling to display the reference image acquired according to the designated constituted data with the infrared thermal image generated by the acquired thermal imaging data together according to the position parameter of the reference image.

A thermal image analyzing step is used for analyzing the thermal imaging data acquired in the acquiring step to acquire an analysis result according to a specified analysis mode, based on the analysis area with the position parameter.

A diagnosing step is used for diagnosing according to a specified diagnosis rule to acquire a diagnosis result according to the analysis result acquired in the thermal image analyzing step.

These and other aspects and advantages of the present invention will be described according to the following description.

BRIEF DESCRIPTION OF THE DRAWINGS

FIG. 3 is a schematic diagram showing body information and constituted data stored in a storage medium;

FIG. 4 is a schematic diagram showing the body information, the constituted data of multiple types, analysis modes, and diagnosis rules stored in the storage medium;

FIG. 10 is a schematic diagram showing a menu setting interface of object processing;

FIG. 11 is a schematic diagram showing a menu setting interface of object computing;

FIG. 12 is a schematic diagram showing five examples of the analysis area acquired by computing or processing;

FIG. 13 is a schematic diagram showing a menu setting interface including a reference image, an analysis area, an analysis mode, and a diagnosis rule;

FIG. 14 is a schematic diagram showing a menu setting interface of switch configuration including the reference image, the analysis area, the analysis mode, and the diagnosis rule;

FIG. 30 is a flow chart showing a diagnosis mode with record processing according to the fourth embodiment;

FIG. 31 is a schematic diagram showing a file format of a thermal image file storing the specified record information associated with infrared data;

FIG. 32 is a schematic diagram showing the infrared thermal image corresponding to the record thermal imaging data when visual matching;

DETAILED DESCRIPTION OF THE INVENTION

This invention may be further described according to the drawings. For better understanding, the following described embodiments do not limit the scope of the invention and can be changed to different forms in the scope of the invention. In the invention, thermal imaging data may be thermal image AD value data (such as the data acquired after AD conversion of output signals of an infrared detector), image data of an infrared thermal image, array data of temperature values, or other data generated based on the thermal image AD value data. In the first embodiment, a thermal imaging device 13 is as an example of a device for diagnosing thermal images.

Figure 1:
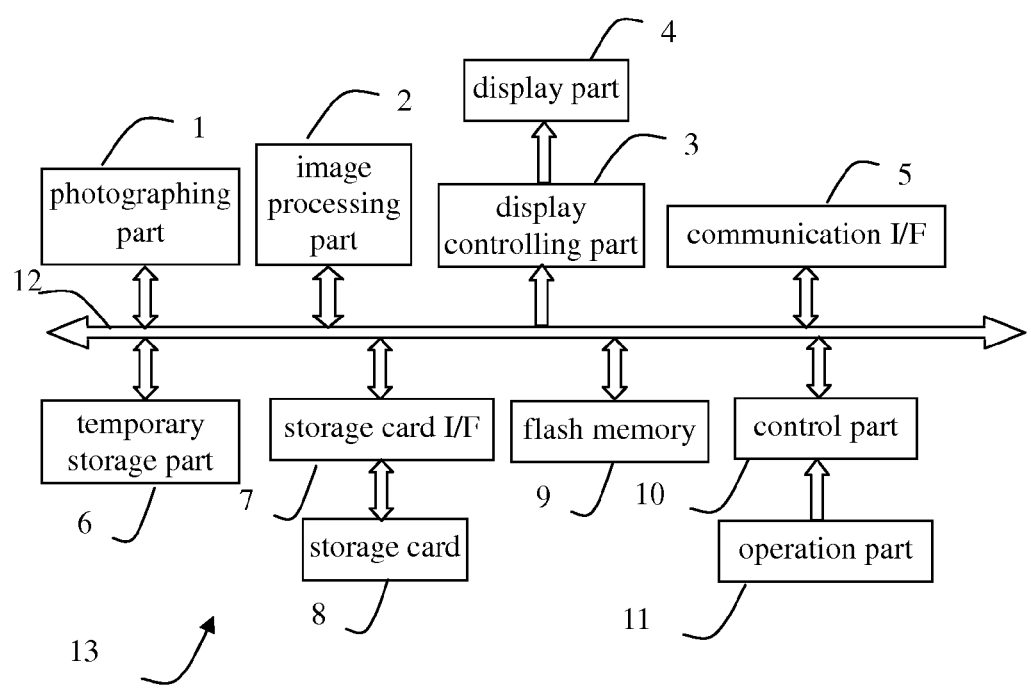
FIG. 1 is a block diagram showing a thermal imaging device according to a first embodiment.

The structure of the thermal imaging device 13 in the first embodiment is described according to FIG. 1. FIG. 1 is a block diagram showing the thermal imaging device 13 according to the embodiment.

The thermal imaging device 13 includes a photographing part 1, an image processing part 2, a display controlling part 3, a display part 4, a communication I/F 5, a temporary storage part 6, a storage card I/F 7, a storage card 8, a flash memory 9, a control part 10, and an operation part 11. The control part 10 is connected with each other part via a control and data bus 12, and is responsible for overall control of the thermal imaging device 13. A CPU, a MPU, a SOC, or a programmable FPGA may realize the control part 10.

The photographing part 1 includes an optical part, a lens driving part, an infrared detector, and a signal preprocessing circuit, which are not shown. The optical part is composed of infrared optical lenses, and is used for focusing received infrared radiation on the infrared detector. The lens driving part drives the lenses to perform focusing or zooming operation according to a control signal of the control part 10, and the optical part may also be manually regulated. The infrared detector such as a refrigerating or non-refrigerated infrared focal plane detector converts the infrared radiation passing through the optical part to electrical signals. The signal preprocessing circuit, including a sample circuit, an AD conversion circuit, and a timing trigger circuit, performs signal processing such as sampling for the electric signals output from the infrared detector in a specified period. The signals are converted to digital thermal imaging data by the AD conversion circuit. The thermal imaging data may be 14-bit or 16-bit binary data (also called AD value).

The image processing part 2 is used for performing specified processing for the thermal imaging data acquired by the photographing part 1. The image processing part 2 performs processing for converting data to be suitable for displaying or recording, such as modification, interpolation, pseudo-color, synthesis, compression, or decompression. The image processing part 2 is used for performing specified processing for the thermal imaging data acquired by the photographing part 1 to acquire image data of the infrared thermal image. For example, the imaging processing part 2 may perform specified processing such as non-uniformity correction or interpolation for the thermal imaging data acquired by the photographing part 1 and then may perform pseudo-color processing for the thermal imaging data after the specified processing, to acquire the image data of the infrared thermal image. In one embodiment of the pseudo-color processing, a corresponding range of a pseudo-color plate may be determined according to a range of the thermal imaging data (AD value) or a setting range of the AD values, and the particular color value to which the thermal imaging data corresponds in the range of the pseudo-color plate is used as the image data of the corresponding pixel position in the infrared thermal image. In the embodiment, gray scaling for the infrared image may be as a special example of the pseudo-color processing. Further, based on a record instruction of the control part 10, the image processing part 2 is used for performing specified compression for the thermal imaging data to acquire compressed thermal imaging data, and then the thermal imaging data is record to a storage medium such as the storage card 8. In addition, the image processing part 2 performs different processing related to image processing, such as increasing and decreasing pixels to change the dimension of the image data, or cutting of the image data. The image processing part 2 may be realized by a DSP, other microprocessors, or a programmable FPGA, or the image processing part 2 may also be integrally formed with the control part 10.

According to the control of the control part 10, the display controlling part 3 allows the display part 4 to display image data for displaying stored in the temporary storage part 6. In detail, the display controlling part 3 includes a VRAM, a VRAM control unit, and a signal generating unit, regularly reads the image data that is read from the temporary storage part 6 and stored in the VRAM under the control of the control part 10 from the VRAM, and generates video signals to be displayed on the display part 4. In the thermal imaging device 13, the display part 4 is as an example of a display part. However, the invention is not limited thereto. The display part may further be other display devices connected with the thermal imaging device 13, and the thermal imaging device 13 may not include the display part in itself. The display controlling part 3 may be integrally formed with the image processing part 2 or the control part 10.

The communication I/F 5 may be an interface for connecting and exchanging data between the thermal imaging device 13 and an external device according to communication specification such as USB, 1394, or network. The external device may be a personal computer, a server, a PDA (personal digital assistant device), other thermal imaging devices, a visible light photographing device, or a storage device.

The temporary storage part 6, such as a RAM or DRAM volatile storage, is a buffer storage for temporarily storing the thermal imaging data output from the photographing part 1, and is a working storage of the image processing part 2 and the control part 10 for temporarily storing the processed data of the image processing part 2 and the control part 10. However, the invention is not limited. A storage or register in the processor such as the control part 10 or the image processing part 2 may also be defined as a temporary storage medium.

The storage card I/F 7 is used as an interface of the storage card 8. The storage card I/F 7 is connected with the storage card 8 as a rewritable non-volatile storage, which can be detachably installed in a groove of the main body of the thermal imaging device 13 and can record the data such as the thermal imaging data according to the control of the control part 10.

The flash memory 9 stores control programs and different kinds of data used in different control.

Figure 2:
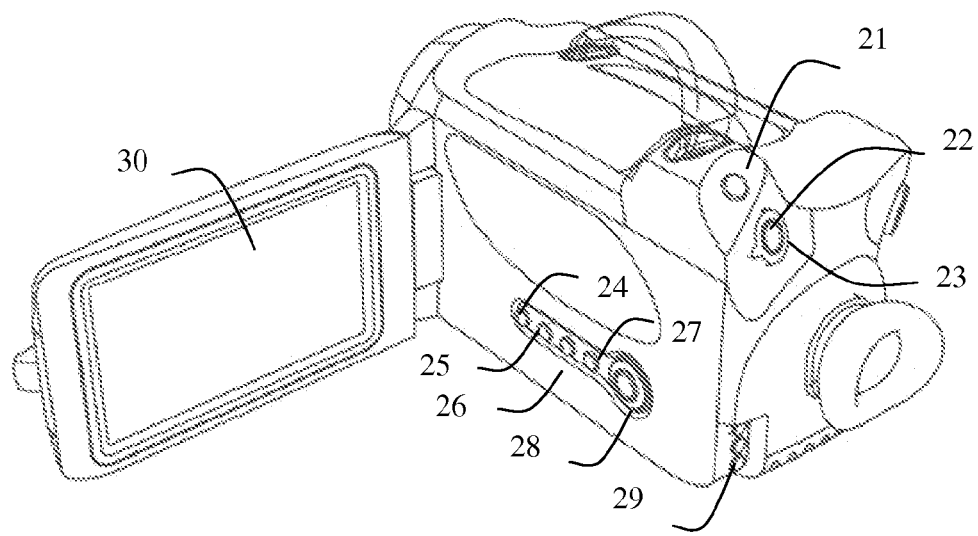
FIG. 2 is an outline diagram showing the thermal imaging device according to the first embodiment.

The operation part 11 is used for a user to perform operation. The control part 10 executes the corresponding program according to an operation signal of the operation part 11. As shown in FIG. 2, the operation part 11 may include a record key 21, a switch key 22, an analysis key 23, a menu key 24, a mode key 25, a processing key 26, an enter key 27, a direction key 28, a position key 29, and a replay key. The record key 21 is used for record operation, the switch key 22 is used for switch operation, the analysis key 23 is used for operation related to analysis and diagnosis, the menu key 24 is used for entering into or exiting from a menu mode, the mode key 25 is used for entering into or exiting from a diagnosis mode, the processing key 26 is used for entering into or exiting from a processing mode, the enter key 27 is used for determining operation, the direction key 28 is used for selecting menu items, and the replay key is used for entering into or exiting from a replay mode. However, the invention is not limited thereto. A touch screen 30 or a phonic part (not shown) may be used for realizing related operation.

The storage medium, reference image, constituted data, morphological constituted data, auxiliary constituted data, analysis area, analysis mode, diagnosis rule, computing object, processing object, main object, specified position and dimension, position parameter, position information, self-adaptive area, and self-adaption are described hereinbelow.

The storage medium may be a storage medium in the thermal imaging device 13, such as a non-volatile storage medium i.e. the flash memory 9 or the storage card 8 and a volatile storage medium i.e. the temporary storage part 6, and may be other storage mediums connected with the thermal imaging device 13 wiredly or wirelessly, such as a storage medium in other devices connected with the communication I/F 5 wiredly or wirelessly, i.e. other storage devices, thermal imaging devices, or computers, or a storage medium in a network destination. Preferably, the data such as the constituted data is prestored in the thermal imaging device 13 or the connected non-volatile storage medium (such as the flash memory 9).

Figure 5:
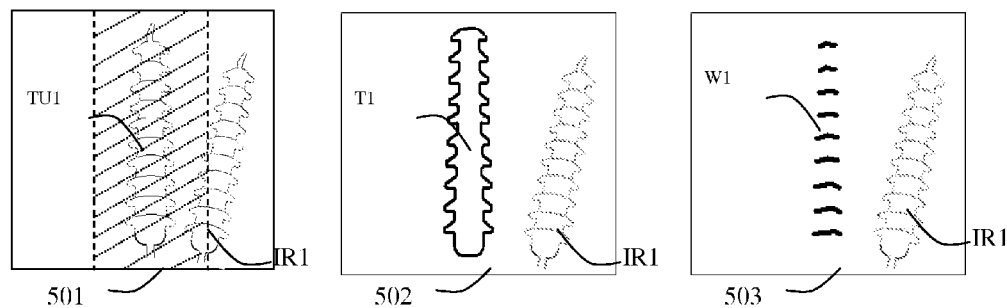
FIG. 5 is a schematic diagram showing examples of a reference image, wherein 501 represents an example of displaying a semitransparent reference image and an infrared thermal image together, 502 represents an example of displaying a reference image of an edge contour of a photographed body and the infrared thermal image together, and 503 represents an example of displaying a reference image of a texture of the photographed body and the infrared thermal image together.

The reference image reflecting morphological characters of a photographed body may be the image of the reference image and the infrared thermal image displayed together in FIG. 5. A reference image TU1 (semitransparent) in 501 reflects the texture and contour of the photographed body, which is vivid for understanding. This reference image, such as a visible light image, an infrared thermal image of a photographed body, and an image with texture and contour characters in advance, is semi transparently displayed. A reference image T1 (an edge contour image which may be opaque or semitransparent) in 502 and a reference image W1 (a texture image which may be opaque or semitransparent) in 503 may be transparent to show the infrared thermal image at other pixels except the superimposed part. In addition, the morphological character may be the morphological character of the whole or local photographed body.

The constituted data is the constituted data related to the reference image and the analysis area, and may be vector image data, lattice data, or data including the vector image data and the lattice data. The lattice data may be lattice image data or the lattice data of the thermal imaging data. The constituted data may be divided into the morphological constituted data and the auxiliary constituted data. The constituted data for acquiring the reference image reflecting the morphological characters of the photographed body in FIG. 5 is called the morphological constituted data, and the reference image reflecting the morphological character may be acquired by one or more morphological constituted data or the morphological constituted data combined with the auxiliary constituted data. The constituted data for acquiring the reference image reflecting the morphological character may be one or more and at least include one morphological constituted data.

Figures 6, 7, 8:
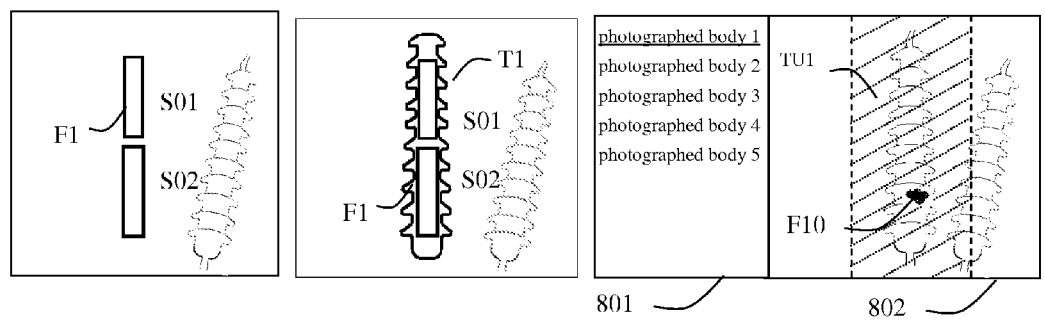
FIG. 6 is a schematic diagram showing an example of displaying an analysis area and an infrared thermal image together in the prior art.
FIG. 7 is a schematic diagram showing an example of displaying a reference image (including an analysis area and an edge contour image) and an infrared thermal image together.
FIG. 8 is a schematic diagram showing an example of displaying a reference image including an analysis area F10 acquired by processing and a semitransparent image TU1 and an infrared thermal image together.

In the embodiment, the constituted data except the morphological constituted data is called auxiliary constituted data, which may be used for generating an analysis area. In FIG. 6, an analysis area F1 is an analysis area set in the prior art, with weak reference for photographing when used alone. In addition, during record processing, the auxiliary constituted data is related and stored with the thermal imaging data. Since the data volume of the morphological constituted data is large, the storage of the auxiliary constituted data of an auxiliary object having a specified position relation with the reference image may reduce the stored data volume. When the object acquired by the auxiliary constituted data represents the analysis area, the storing mode facilitates the subsequent batch processing.

Preferably, the reference image is acquired by the morphological constituted data and the auxiliary constituted data together. For example, a contour image T1, an analysis area F1, and an infrared thermal image in FIG. 7 are displayed together, thereby providing a prompt to improve the reference effect of T1 and to avoid the weak reference of F1.

In the embodiment, the storage medium at least stores one morphological constituted data. The constituted data may be stored in the storage medium in a way that one constituted data corresponds to one file such as a data file, a thermal image file, an image file, or a graph file, may be stored in the storage medium after processed in an external computer, or may be stored in the storage medium after being acquired according to the thermal imaging data photographed by the thermal imaging device 13 or the data after specified processing. The constituted data may be stored in a database, and the constituted data may be correspondingly stored to a specified field. In addition, the multiple constituted data may be stored in one data file. Preferably, the auxiliary constituted data and the morphological constituted data is related and stored in the storage medium, and a specified position relation between the objects acquired by the auxiliary constituted data and the morphological constituted data is stored. The auxiliary constituted data may be as attribute data of the morphological constituted data.

The analysis area corresponds to the part in the infrared thermal image to be analyzed, such as area units i.e. points, lines, or planes, or a combination of the multiple area units. In the embodiment, the analysis area may be acquired according to the morphological constituted data or the auxiliary constituted data. Preferably, the constituted data prestored in the storage medium may be used for determine the analysis area. In addition, the analysis area may be acquired by a designated processing object combined with a processing algorithm or by computing a designated computing object according to a specified algorithm.

One embodiment of the constituted data stored in the storage medium is described according to a table in FIG. 3 (called Table 3 hereinbelow). That is, multiple body information and one morphological constituted data related to each body information is stored. The multiple body information and the morphological constituted data (the constituted data of T1 or the constituted data of T2) to which each body information corresponds is related via Table 3. In addition, if the relevance is built via index information (such as a file name) of the morphological constituted data stored in Table 3, the storage medium further stores files of the morphological constituted data to which the index information (such as the file name) corresponds. The body information is the information related to a photographed body, such as the information representing a position, a type, a number, a name of the photographed body, or a combination thereof. In Table 3, some different body information (such as, a photographed body 2 and a photographed body 3 in Table 3) is related to the same constituted data. In an occasion of infrared detection, there are a lot of different photographed bodies with the same shape. As the morphological constituted data is stored and related with the body information in Table 3, a user can select the constituted data according to the body information recognized on the scene, thereby avoiding confusion caused by incorrect selection of the constituted data and reducing redundant data.

According to a table in FIG. 4 (called Table 4 hereinbelow), another preferred embodiment of the constituted data stored in the storage medium is described. That is, multiple body information and multiple constituted data related to the each body information may be stored. In Table 4, the multiple constituted data (the type of the morphological constituted data includes a benchmark 1 and a benchmark 2, the type of the auxiliary constituted data includes an auxiliary 1) related to the multiple body information, analysis mode information of "analysis mode 1" when the constituted data of the auxiliary 1 acquires the analysis area, the analysis mode information of "analysis mode 2" when the constituted data of each type acquires the analysis area, "diagnosis rule 1" to which the "analysis mode 1" corresponds, and "diagnosis rule 2" to which the "analysis mode 2" corresponds are related via Table 4. The information (not shown) of a specified position relation between the objects acquired by the constituted data related to the same body information is stored. The object acquired by the constituted data may be the reference image or special points, lines, planes representing the analysis area acquired by the constituted data. The specified position relation is a specified relative position relation. In detail, for example, in an original storing state (in a state without displacement, scaling, or rotation), it is the position information (information of coordinate positions, dimensions, or rotating angles) of the object acquired by the constituted data of the benchmark 2 and the auxiliary 1 related to the same body information, relative to the object acquired by the constituted data of the benchmark 1. In addition, the specified position relation may be the position information (the information of coordinate positions, dimensions, or rotating angles) of the stored objects in the same reference frame (such as in an infrared thermal image). In Table 4, the information of the specified position relation is as one attribute of the constituted data, or may be stored alone. In addition, if the relevance is built via the index information (such as a file name) of the constituted data stored in Table 4, the file of the constituted data to which the index information (such as the file name) corresponds may be further stored in the storage medium. In Table 4, the constituted data of different types is classified and stored according to a specified type, such as, according to display effects of the objects acquired by the constituted data. That is, the benchmark 1 corresponds to the contour, the benchmark 2 corresponds to the infrared thermal image (such as a local standard body thermal image) processed in advance, and the auxiliary 1 corresponds to a focused attention area. In addition, classification may be performed according to a photographing use or a data type (the vector image data, lattice data). In addition, the classification is not limited to the single constituted data and may be performed for a combination of multiple constituted data. In addition, the invention is not limited to the embodiment in Table 4. For example, the storage medium may store the constituted data via graph files, image files (for example, the file name includes the corresponding body information), and the files may be classified via file folders.

Although the information of the specified position relation between the objects acquired by the constituted data related to the same body information is prestored in the storage medium (the flash memory 9) in the embodiment of Table 4, it may not be stored. For example, users may give the specified position relation between the objects, or the specified position relation between the objects may be set according to a default position rule of the thermal imaging device 13. In addition, the specified position relation between the constituted data acquired by computing and processing and other objects and between the constituted data acquired by computing and/or processing a designated object and the designated object may be determined by a corresponding computing or a processing rule. For example, the specified position relation between the contour and the analysis area acquired after scaling and deforming the contour may be determined according to a base point of scaling and deforming, a scaling ratio, and a deforming ratio. In the following text, the specified position relation between the objects acquired by the constituted data is sometimes also called the specified position relation between the constituted data.

The specified position relation of the objects (or the constituted data) is described as an example of two objects. As the specified position relation between the two objects is unchanged, according to a position parameter (a position, a dimension, or a rotating angle) of one object in an infrared thermal image, the position parameter (the position, the dimension, or the rotating angle) of the other object in the infrared thermal image may be set. When one of the objects performs a displacement, the other object also performs the same displacement, to remain the relative position therebetween. When one of the objects performs dimension scaling, the other object performs the same dimension scaling based on the same base point, to remain the same dimension scale. When one of the objects performs angle rotation, the other object rotates the same angle based on the same base point, to remain the same relative rotating angle. In a special condition, as one object is a feature point (a feature coordinate point) of the other object, when the other object performs a displacement, the feature point performs the same displacement; when the other object scales relative to a scaling base point, by using the scaling base point as a coordinate origin, the coordinate (X2, Y2) of the feature point relative to the scaling base point after scaling is equal to a product (X1*S, Y1*S) of the coordinate (X1, Y1) of the feature point relative to the scaling base point before scaling and a scaling ratio S; when the other object rotates an angle P (such as anticlockwise), the feature point rotates the same angle based on the same rotating base point, and the relation between the coordinate (X2, Y2) of the feature point relative to the rotating base point after rotation and the coordinate (X1, Y1) of the feature point relative to the rotating base point before rotation is (X2, Y2)=(X1 cos P−Y1 sin P, Y1 cos P+X1 sin P).

The analysis mode represents an analysis computing rule used when specified analysis is performed for the thermal imaging data determined on the analysis area to acquire an analysis result. For example, the analysis mode may be to compute the maximum temperature, the average temperature, the minimum temperature, or the percentage ratio, and may include a computing relation between different area units, such as the difference in temperature. However, it is not limited to the temperature value computing, and may also relate to analysis computing rules of different analysis related to the thermal imaging data or the infrared thermal image.

Preferably, the analysis mode information related to the analysis mode is related and stored with the corresponding constituted data in the storage medium, which may be used when the constituted data acquires the analysis area (the relevance method is that the analysis mode or the diagnosis rule may be as the attribute information of the constituted data), thereby facilitating to prepare the complicated analysis area and analysis mode for analysis with simple operation. With regard to different body information, the analysis mode information may be different in direct to the same or different constituted data. In FIG. 4, with regard to "analysis mode 1" related to the constituted data of "auxiliary 1", the information (the analysis mode information of F1) of the analysis mode 1 of a photographed body 1 is to compute the maximum temperature of an area unit S01, the maximum temperature of an area unit S02, and the difference of the maximum temperature of the area units S01 and S02 (the analysis area F1 acquired by the constituted data of F1 includes area units S01, S02). The information (the analysis mode information of F2) of the analysis mode 1 of a photographed body 2 is to compute the average temperature, the maximum temperature in the area (the analysis area F2 acquired by the constituted data of F2), and the difference of the maximum temperature and the average temperature. With regard to different body information, the analysis mode information may be universal to the same or different constituted data. For example, the information of the analysis mode 2 is to compute the maximum temperature, the average temperature in the analysis area acquired by the determined constituted data, and the difference of the maximum temperature and the average temperature, which may be universal for all of the constituted data in Table 4 and may be as the analysis mode related to the constituted data of different types in Table 4.

The diagnosis rule is provided for the diagnosing part to diagnose according to the specified diagnosis rule to acquire a diagnosis result according to the analysis result acquired by the thermal image analyzing part. Preferably, the diagnosis is performed according to the diagnosis rule related to the analysis mode. For example, the diagnosis may be performed according to the diagnosis rule acquired according to the diagnosis rule information related and prestored with the analysis mode information corresponding to the analysis mode related to the analysis.

A diagnosis rule 1 related to an analysis mode 1 is taken for example. The information (a diagnosis rule of F1) of the diagnosis rule 1 includes at least one diagnosing comparing relation and a diagnosis threshold corresponding to the analysis mode 1 (an analysis mode of F1). Further, in the electric power industry, the diagnosis result is expected to acquire directly, and there are corresponding diagnosis thresholds and results for the normal, attention, and defect condition of the photographed body (may be one or more than three conditions). For example, the diagnosis rule 1 (the diagnosis rule of F1) of the photographed body 1 may include the followings:

1) normal: the difference between the maximum temperature of S01 and S02 may be smaller than 2□; (normal: S01MAX−S02MAX<2□ or S02MAX−S01MAX<2□)

2) attention: the difference between the maximum temperature of S01 and S02 may be smaller than or equal to 4 □ or greater than or equal to 2□; (attention: 2□≤S01MAX−S02MAX≤4□ or 2□≤S02MAX−S01MAX≤4□)

3) defect: the difference between the maximum temperature of S01 and S02 may be greater than 4□. (defect: S01MAX−S02MAX>4□ or S02MAX−S01MAX>4□)

Obviously, the same analysis mode may correspond to one or more diagnosis rule. Preferably, the analysis mode may be related and stored with the corresponding diagnosis rule. Further, the diagnosis rule may be related with the diagnosis basis, the detailed defect type, the defect extent, and the processing suggestion, corresponding to the result. The diagnosis rule 2 related to the analysis mode 2 is that the difference between the maximum temperature and the average temperature in analysis area smaller than 3□ is normal and the other is defect. The analysis mode 2 and the diagnosis rule 2 may not be related and stored with the body information and the constituted data in Table 4, and may be stored in the storage medium of the thermal imaging device 13 as the universal analysis mode and diagnosis rule.

In detail, for example, the control part 10 (as the diagnosing part) compares the analysis result acquired by analysis and the diagnosis threshold in the diagnosis rule corresponding to the analysis mode according to the comparing relation in the diagnosis rule, to acquire the diagnosis result. The output of the diagnosis result may be control signals. For example, the control part 10 may be as an informing control part via display changes of words or images (including the infrared thermal image and the reference image) on the display part, light generated by the guiding lights, sound prompt, or vibration, as long as the users can be informed. Preferably, the display part 4 may be controlled to display the diagnosis result. Further, the diagnosis threshold, the diagnosis basis, the defect type, the defect extent, and the processing suggestion related to the diagnosis may be informed in a way that the users can know, such as words. Correspondingly, the related data is related and stored with the data of the diagnosis rule.

The processing object can acquire the morphological constituted data via processing according to a specified processing rule. The processing object may be the morphological constituted data stored in the storage medium, such as the morphological constituted data of "benchmark 1" and "benchmark 2" in Table 4, or may be the thermal imaging data acquired from the thermal image file in the storage card 8 or acquired by photographing. The processing object and the processing rule may be configured in advance. Preferably, the processing rule at least includes the image processing for the processing object, such as "cutting", "threshold range extracting", "edge extracting", or a combination thereof. The processing may be specified image processing for the processing object, such as cutting, feature extracting (such as threshold range extracting, edge extracting), enhancing, filtering, pseudo-color, color adjustment, or a combination thereof.

The cutting is to extract data of the processing object located in a cutting area.

The threshold range extracting is to extract data of the processing object located in a threshold range. The threshold range may be an AD value range of the thermal imaging data, a color-code range of the infrared thermal image, a threshold range of the temperature, a gray-scale range, a luminance range, or a color range, and it may be prestored or may be set or adjusted by the users. The threshold range extracting may be to extract a temperature band or a color band in the infrared thermal image (the processing object) to acquire the morphological constituted data, to extract pixels of specified colors in a visible light image (the processing object) to acquire the morphological constituted data, or to extract pixels of specified AD values in the thermal imaging data (the processing object) to acquire the morphological constituted data.

The edge extracting is to extract data of the edge contour based on the processing object according to a specified algorithm. For example, binaryzation may be performed for the infrared thermal image (the processing object) according to a specified threshold range. The specified threshold range may be a prestored threshold range, or the binary threshold range may be set manually as a binary image is displayed. The threshold range may be a set AD value range of the thermal imaging data, a threshold range of the temperature, a gray-scale range, or a color-code range. Then, a connected region of the image after the binaryzation is processed. Then, an edge detecting processing is performed for the connected region, thus to acquire edge contour data. Further, vectorization is performed for the acquired edge contour data. Other detailed processing methods may adopt mature methods in the field, and they are not described in detail.

The computing object can acquire auxiliary constituted data via computing according to a specified computing rule. The computing object may be "benchmark 1", "benchmark 2", "auxiliary 1", or a combination thereof in Table 4. The computing rule at least includes scaling, deforming, dividing, halving, computing a bounding rectangle, computing an inscribed rectangle, computing a center line, computing a feature point, computing an enveloping line, or a combination thereof for the computing object. In addition, the user can designate the computing object according to the selection of the reference image or a synthesis object displayed on the display part 4, or designate from the constituted data of points, lines, or planes having the specified position relation with the reference image.

The specified position and specified dimension are the position and dimension of the reference image located in the infrared thermal image or further include the rotating angle. They may be parameters of the specified position and the specified dimension in a coordinate system of the display part (a display screen) (still in a display window of the infrared thermal image), or may be parameters of the specified position and specified dimension in a coordinate system of the infrared thermal image in the display window of the infrared thermal image. Further, a position setting part (the control part 10) only sets the position of the reference image located in the infrared thermal image, and the display dimension is the default original dimension, which is also considered as setting of the specified position and specified dimension.

With regard to the reference image reflecting the morphological characters, the position parameter is the specified position and specified dimension of the reference image located in the infrared thermal image. With regard to the analysis area, the position parameter is the position (for example, the analysis area is a point), the dimension, or the rotating angle of the analysis area located in the infrared thermal image. In the embodiment, the position parameter may be the position parameter in the coordinate system of the display part (the display screen) (still in the display window of the infrared thermal image), or may be the position parameter in the coordinate system of the infrared thermal image in the display window of the infrared thermal image.

The position information, such as the position information related to the constituted data, may be the information of the position parameter, or the information of the rule for acquiring the position parameter.

When there is multiple constituted data with the specified position relation (related to the reference image), the main object is the object acquired by one or multiple constituted data designated therefrom. When the main object is designated, the position setting part is used for setting the position parameter of the main object in the infrared thermal image, and then for setting the position parameter of the other object in the infrared thermal image according to the position parameter of the main object in the infrared thermal image and the specified position relation between the other object and the main object.

The self-adaptive area is a specified area in the infrared thermal image. For example, in the embodiment, in the infrared thermal image, 90% of a centering window area Z1 of the infrared thermal image may be the self-adaptive area.

The self-adaption is the position setting embodiment that the non-overflow maximization scaling with a fixed aspect ratio in a self-adaptive area is performed for a self-adaptive object at a designated position (or including a specified rotating angle) in the self-adaptive area to acquire the dimension after self-adaption, thus to acquire the specified position and specified dimension of the self-adaptive object located in the infrared thermal image. The embodiment of the self-adaptive object centered and self-adapted in Z1 is taken for example. The ratio of the X axis and the ratio of the Y axis between the self-adaptive area Z1 (the dimension X1, Y1) and the self-adaptive object (the original dimension X2, Y2 of the self-adaptive object) are computed, and the smaller ratio between X1/X2 and Y1/Y2 is selected as a scaling ratio of the self-adaptive object during centering based on a center point of the self-adaptive object, thereby acquiring the position parameter of the self-adaptive object located in the infrared thermal image. The self-adaptive object may be the analysis area or the reference image. The position parameter is set via self-adaption, thereby facilitating to standardize and adjust the position parameter of the analysis area or the reference image located in the infrared thermal image. In the following embodiments, the mentioned self-adaption is with the example that the self-adaptive object is centered and self-adapted in Z1.

According to different embodiments of display control, the reference image displayed with the infrared thermal image may be one or include multiple synthesis objects synthesized with the infrared thermal image. The single synthesis object may be acquired by one or multiple constituted data. When the multiple constituted data is used to acquire one synthesis object, the position setting part may only set the specified position and specified dimension of the synthesis object located in the infrared thermal image and is not necessary to set the position parameter of the object located in the infrared thermal image acquired by each of the constituted data, respectively. When the reference image includes multiple synthesis objects, the position setting part may set the position parameter of each synthesis object located in the infrared thermal image, respectively.

The detailed operation and control flows of the first embodiment are described in detail hereinbelow. In the embodiment, supposing that the flash memory 9 stores the contents as shown in FIG. 4, the applied scene may be to photograph bodies in a substation. When the power is on, the interior circuits of the control part 10 are initialized, and then a standby photographing mode is entered, that is, the photographing part 1 acquires thermal imaging data, the image processing part 2 performs specified processing for the thermal imaging data acquired by the photographing part 1 to store in the temporary storage part 6, and the control part 10 controls the display controlling part 3 to allow the display part 4 to continuously display the infrared thermal image in a dynamic image mode. In the state, the control part 10 continuously monitors whether other modes are switched according to the predetermined operation or shutdown operation is performed. If yes, corresponding processing control is performed.

Figure 9:
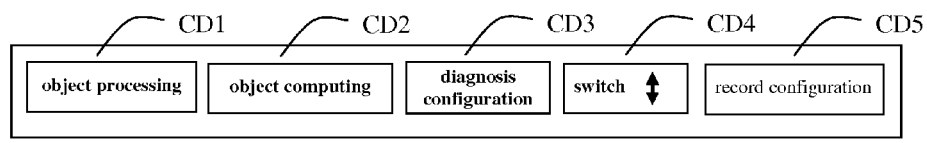
FIG. 9 is a schematic diagram showing a setting menu of the thermal imaging device according to the first embodiment.

When a user presses a menu key, a menu mode is entered, and the display part 4 displays a menu as shown in FIG. 9. When the menu item therein is selected, the corresponding configuration interface is displayed. The configuration part includes the control part 10 and the operation part 11. In response to operation signals of the users, the control part 10 performs corresponding display control.

Referring to the configuration interface in FIG. 10, the menu item "object processing CD1" is described, which is provided for users to assign a processing object and to set (increase, amend, or delete) a processing rule.

The constituted data CD11 displays the information of the constituted data to be selected. The information of the constituted data to be selected may be type information of "benchmark 1" and "benchmark 2" acquired from Table 4. In addition, the type information to be selected may be other type information such as the type information of the constituted data that the designated processing object combined with the specified processing rule represents.

The processing object CD12 is provided for users to select the constituted data as the processing object. Obviously, one or more morphological constituted data may be selected as the processing object.

The processing rule CD13 is provided for users to set the processing rule of the processing object. The processing rule includes processing algorithms and related parameters. When the enter key is pressed at length as the processing algorithm is selected, a parameter bar is displayed for inputting the parameter (not shown).

Referring to the configuration interface in FIG. 11, the menu item "object computing CD2" is described, which is provided for users to select a computing object and to set (increase, amend, or delete) a computing rule.

The constituted data CD21 displays the information of the constituted data to be selected. The information of the constituted data to be selected may be type information such as "benchmark 1", "benchmark 2", or "auxiliary 1" acquired from Table 4. In addition, the type information to be selected may be other type information such as the type information which the designated computing object combined with the specified computing rule represents, or the type information "benchmark 1 (processing)" which the designated processing object combined with the specified processing rule represents.

The computing object CD22 is provided for users to select a computing object. One or more constituted data may be selected as the computing object, and the constituted data acquired by processing the processing object may be as the computing object.

The computing rule CD23 is provided for users to select and set the computing rule of the computing object. The computing rule includes algorithms and related parameters. The algorithm may be scaling, deforming, computing a feature point, halving, computing a bounding rectangle, computing an inscribed rectangle, computing a center line, or computing an enveloping line. The parameter may be parameters related to the algorithms such as a scaled base point and a scaling ratio, a deformed base point and a deforming ratio (such as an aspect ratio), a computing parameter of a feature point (such as computing a center point of a contour), a type (such as points, lines, or planes) of the constituted data and dimension set according to the feature point, or a halving number. When the enter key is pressed at length as the algorithm is selected, a parameter bar is displayed for inputting the parameter (not shown). One or more computing rule may be selected for the selected computing object.

Referring to FIG. 12, the function and effect of the analysis area acquired by computing and/or processing are described.

Referring to FIG. 12 (101), the constituted data of the contour T1 as a computing object is scaled and deformed to acquire an analysis area F101 by using a center point of the contour T1 as a base point, which may be used for analyzing and computing temperature distribution of a specified area on the main part of the photographed body, thereby reducing influence of surrounding environment on assessment.

Referring to FIG. 12 (102), the constituted data of the contour T1 is as the computing object, and the algorithm parameter is eight-equal part, to acquire the eight-equal analysis area F102, which is used for analyzing temperature distribution of different sections of the main part of the photographed body.

Referring to FIG. 12 (103), the constituted data of the contour T1 is as the computing object, and the algorithm parameter is to compute a bounding rectangle, to acquire a bounding rectangle F103, which is used for analyzing and measuring the maximum temperature of the photographed body, thereby reducing influence of high-temperature bodies in the background.

Referring to FIG. 12 (104), the constituted data of TU1 (TU1 is a local infrared thermal image) is as the processing object, and the processing rule may be edge contour extracting, to acquire an analysis area F104 of the edge contour, which may be used for analyzing and measuring the maximum temperature of the photographed body, thereby reducing influence of high-temperature bodies in the background.

Referring to FIG. 12 (105), the constituted data of TU1 (TU1 is a local infrared thermal image) is as the processing object, and the processing rule may be to extract pixel points (threshold range extracting) above a specified temperature threshold, to acquire an analysis area F105, which may be used for analyzing and computing feature parts of the photographed body.

Obviously, the designated object may be processed and/or computed to acquire the constituted data. In addition, the configuration menus of "object processing CD1" and "object computing CD2" may be merged to one configuration menu. One or more processing rule and/or one or more computing rule may be selected for the designated object (the constituted data prestored in FIG. 4, the thermal image file in the storage card 8, the thermal imaging data acquired via photographing), and the processing and/or computing is collectively called processing for the designated object. In addition, the related processing rule or computing rule may be configured without directing to the specified constituted data, which may be as the default configuration suitable for the subsequent selected constituted data.

Referring to the configuration interface in FIG. 13, the configuration of "diagnosis configuration CD3" is described.

The "diagnosis configuration CD3" is provided for users to set a specified designated type, a position rule, a synthesis parameter, an analysis mode, or a diagnosis rule of the constituted data related to the reference image or the analysis area under a non-switch state in the diagnosis mode by users.

The constituted data CD31 displays the information of the constituted data to be selected, such as the type information "benchmark 1", "benchmark 2", or "auxiliary 1" acquired from Table 4. In addition, other type information, such as the type information "benchmark 1 (processing)" which the processing object set in "object processing CD1" combined with the specified processing rule represents, or the type information "benchmark 1 (computing)" which the computing object set in "object computing CD2" combined with the specified computing rule represents, may also be displayed for selection.

The reference image CD32 is provided for users to select the constituted data for acquiring the reference image. One or more constituted data may be selected to acquire the reference image. In the embodiment, the object acquired by each constituted data is as one synthesis object. That is, when the multiple constituted data is selected, the reference image includes multiple synthesis objects. When the reference image CD32 is selected and the enter key is pressed at length, the part or whole of the selected constituted data may be as one synthesis object (not shown).

The position rule CD33 is used for configuring the position rule related with the position parameter of the reference image and the analysis area located in the infrared thermal image by users.

The constituted data for acquiring the main object is selected. As shown in FIG. 12, the main object may be selected from the constituted data CD31, and may be the main object acquired by the constituted data of the reference image. That is, the constituted data for acquiring the main object may be one or more constituted data with the specified position relation, such as the morphological constituted data and/or the constituted data related to the morphological constituted data. In addition, the computing object designated in the morphological constituted data or the related constituted data is combined with a specified computing rule to acquire the main object, or the processing object designated in the morphological constituted data is combined with a specified processing rule to acquire the main object. Usually, the set main object represents the focused observed area. By exchanging the main object, the exchange of the reference image in different display positions can be realized, thereby realizing different photographing aims. In addition, the user may select the reference image (one or more synthesis objects therein) displayed on the display part 4 as the main object.

When the main object is designated, according to the specified position relation between the other object and the main object and the position parameter of the main object located in the infrared thermal image, the position parameter of the other object located in the infrared thermal image may be set. When there is no designated main object, the position parameter of the object acquired by the constituted data selected in the "reference image CD32" and "analysis area CD35" is set according to the respective position rule.

The self-adaption is used for configuring a position setting mode of the self-adaption and designating a self-adaptive object. By selecting the self-adaption and pressing the enter key at length, the position, dimension, and rotating angle of the self-adaptive area located in the infrared thermal image may be set, and the position and rotating angle of the self-adaptive object located in the self-adaptive area may be set. In the embodiment, 90% of a centering window area of the infrared thermal image is as the self-adaptive area, which is called Z1 for short, and the self-adaptive object is centered and self-adapted in Z1. The self-adaptive object may be selected from the constituted data CD31.

The designated position is used for configuring the position parameter of the object acquired by the selected constituted data located in the infrared thermal image by users. When the user selects the "designated position bar", an input bar (not shown) is displayed, and the user can input the position, dimension, and rotating angle of the object acquired by the selected constituted data located in the infrared thermal image. When the above is not input, the position origin may be defaulted as a top-left corner of the infrared thermal image, the dimension is an original dimension, and the rotating angle is zero.

When the relevance is selected, the position parameter of the object acquired by the constituted data located in the infrared thermal image is acquired, according to the position information related to the selected constituted data in advance.

The synthesis parameter CD34 is used for configuring the synthesis parameter of the reference image acquired by the selected constituted data and the infrared thermal image. The synthesis parameter may be a transparency ratio, a color, a line-type (not shown), a synthesis sequence when the reference image includes a plurality of synthesis objects, or the synthesis parameter related to the constituted data.

Figure 15:
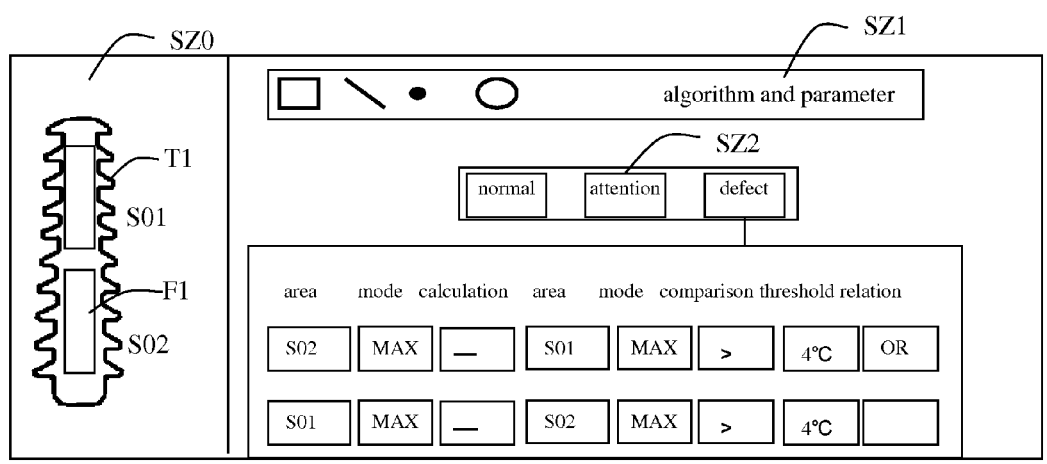
FIG. 15 is a schematic diagram showing a menu setting interface of the analysis mode and the diagnosis rule to which the analysis area corresponds.

The analysis area CD35 is provided for users to configure the type of the analysis area. The user can select the constituted data for acquiring the analysis area from the constituted data CD31. In addition, when the "analysis area CD35" is selected and the enter key is pressed at length, the configuration interface as shown in FIG. 15 is displayed, which is provided for the users to set the analysis area of "point", "line", "plane" in the reference image or the infrared thermal image. In addition, the range of the analysis area may be set. Taking an example of T1 in FIG. 15, the analysis area may be located in the area of T1, out of the area of T1, or on the edge contour of T1.

The constituted data of the analysis area may be acquired according to the morphological constituted data stored in the storage medium or the constituted data related to the morphological constituted data, or may be acquired by corresponding processing for the designated object in the morphological constituted data stored in the storage medium or the related constituted data according to the specified computing rule and/or processing rule. One or more constituted data is selected to acquire the analysis area. In addition, the analysis area of "point, line, plane" may be manually operated, which may be set according to the reference image, thereby the set analysis area facilitating subsequent use. The user may select the setting mode of the analysis area according to aims of infrared detection. When the analysis area is configured, the area units in the analysis area may be numbered manually or automatically (F1 in FIG. 15 includes frame area units S01, S02), or the prestored constituted data has the respective number, using as the number of the analysis area. When the configuration of the analysis area is finished, the analysis mode to which the analysis area corresponds and the diagnosis rule to which the analysis mode corresponds may be further configured.

The analysis mode and diagnosis rule CD36 is provided for users to configure the analysis mode to which the analysis area corresponds and the diagnosis rule to which the analysis mode corresponds. The information to be selected may be the analysis diagnosis 1 (the analysis mode 1 and the related diagnosis rule 1), the analysis diagnosis 2 (the analysis mode 2 and the related diagnosis rule 2), or information of other analysis mode and diagnosis rule stored in advance in Table 4. In addition, when the "analysis mode and diagnosis rule CD36" is selected and the enter key is pressed at length, the configuration interface as shown in FIG. 15 is displayed.

Referring to FIG. 15, the configuration interface of the analysis area, the analysis mode, and the diagnosis rule, including an adjusting bar SZ0 of the analysis area, an analysis area setting bar SZ1, and a setting bar SZ2 of the analysis mode and the diagnosis rule, is described. A photographed body 1 is taken for example.

In the adjusting bar SZ0, for adjusting the specified position relation between the analysis area and the reference image, the reference image and the analysis area are displayed for adjustment, such as, the reference image T1 (benchmark 1) selected in "reference image CD32" and the analysis area F1 (auxiliary 1) selected in "analysis area CD35" in the embodiment. In the adjusting bar SZ0, the users can perform operation, such as decreasing, changing positions, adjusting, changing types (point, line, plane), or setting new area units for the area units S01, S02 in the analysis area F1.

The analysis area setting bar SZ1 is used for setting the analysis area to which the reference image T1 corresponds, such as points, lines, planes, or the similar computing rule in "object computing CD1". At that moment, the computing object is usually defaulted as the reference image T1.

The diagnosis rule setting bar SZ2 is used for setting the analysis mode and the diagnosis rule. The "area" is used for selecting a number of the area unit displayed in SZ0, such as S01, S02, the "mode" may be maximum, minimum, or average temperature, the "calculation" may be addition, subtraction, multiplication, or division, the "comparison" may be a comparing relation such as greater or smaller, the "threshold" may be a threshold for diagnosis, and the "relation" may be logic relation of AND, OR, NOT. In addition, there may be an information selecting or inputting bar (not shown) for inputting the diagnosis basis, a defect type, a defect extent, and a processing proposal.

When "comparison" and "threshold" are not input, the analysis mode is formed, and when the "comparison" and "threshold" are input, the analysis mode and the corresponding diagnosis rule (or may be understood as the diagnosis rule with the analysis mode) are formed. When the setting is finished and determined, the constituted data of the reference image T1, the constituted data of the analysis area, the specified position relation therebetween (such as the position parameter of the analysis area F1 in the reference image T1), the analysis mode to which the analysis area corresponds, and the diagnosis rule to which the analysis mode corresponds may be related and stored in the record medium, such as Table 4 in the flash memory 9.

The switch CD4 is used for setting the configuration information related to a switch object when the switch key is pressed once in the state of displaying the reference image configured in "diagnosis configuration CD3" and the infrared thermal image together in the diagnosis mode. Referring to the configuration interface as shown in FIG. 14, the configuration of "switch CD4" is described. The switched configuration information may be the type of the switched constituted data of the reference image, the synthesis parameter (such as a superimposed sequence, a transparency ratio, or a color), a type of the constituted data of the analysis area, the position rule, the analysis mode, the diagnosis rule, or a combination thereof. That is, the change of any item in CD31 to CD39 in FIG. 14, the diagnosis configuration with different using effects may be acquired. As the detailed configuring items are similar to that of "diagnosis configuration CD3", the description is omitted. The difference is that the infrared thermal image may be as the switch object. An arrow in the switch CD4 is used for setting (increasing, amending, deleting) a switch rule. For example, the next switch interface may be entered via the arrow, thereby configuring the configuration information of more switch objects.

Figures 28, 29:
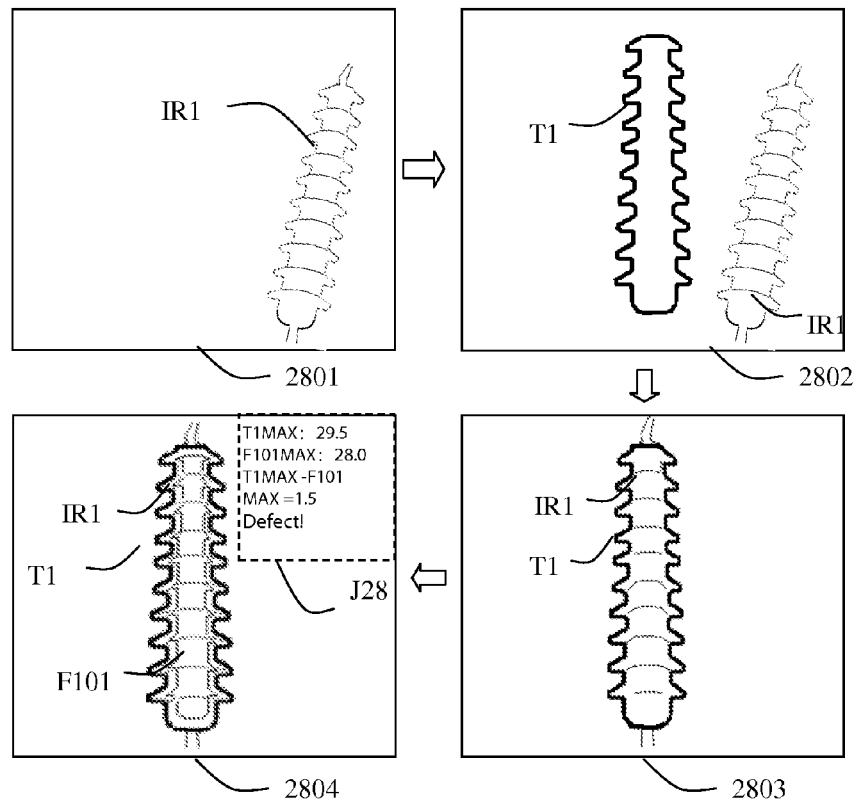
FIG. 28 is a schematic diagram showing display interfaces in the process of photographing the photographed body 1 via the reference image and the diagnosing process according to the third embodiment.
FIG. 29 is a schematic diagram showing a menu setting interface of specified record information according to a fourth embodiment.

Referring to the configuration interface in FIG. 29, the "record configuration CD5" is provided for users to record the specified record information related and stored with the infrared data. The specified record information is the record information that is specified. The specified record information may be the body information, the constituted data, identity information (such as a file name or a number of the constituted data) of the constituted data, the object acquired by the constituted data, the analysis area, the analysis mode, the analysis result, the position information, or a combination thereof.

In the first embodiment, the photographing aim of the user is to detect the global distribution of the thermal field of the photographed body and the focused analysis part (the area represented by the auxiliary 1). To realize the photographing aim conveniently, the configuration is set as shown in FIG.

13. The reference image is "benchmark 1" and "auxiliary 1", the position rule is the benchmark 1 (the main object), the self-adaptive area Z1, and self-adaptive centering, the synthesis parameter is that the transparency ratio is one, the synthesis sequence of the benchmark 1 is one, the synthesis sequence of the auxiliary 1 is two, and the color is defaulted, the analysis area is the auxiliary 1, and the analysis mode and diagnosis rule is the analysis mode 1 and the corresponding diagnosis rule 1 (analysis diagnosis 1).

If there is uncertainty, the user may walk closer to photograph the focused analysis part (the area represented by the auxiliary 1) of the photographed body. The configuration set in "switch CD4" is as shown in FIG. 14. The reference image is "benchmark 1" and "auxiliary 1", the position rule is the auxiliary 1 (the main object), the self-adaption, the self-adaptive area Z1, and centering, the synthesis parameter is that the transparency ratio is one, the synthesis sequence of the benchmark 1 is one, and the synthesis sequence of the auxiliary 1 is two, the analysis area is the auxiliary 1, and the analysis mode and diagnosis rule is the analysis mode 1 and the corresponding diagnosis rule 1 (analysis diagnosis 1).

When the switch key is pressed once, the displaying of "benchmark 1 (main object), auxiliary 1" and the infrared thermal image together is switched to the displaying of "benchmark 1, auxiliary 1 (main object)" and the infrared thermal image together. When the switch key is pressed again, the display state returns to the displaying of "benchmark 1 (main object), auxiliary 1" and the infrared thermal image together. As the different main objects are used, different control modes of the attention focus are entered.

In the first embodiment, part of the constituted data in Table 4 may be used for configuring the reference image and the analysis area. However, according to the description of the menus in FIG. 9 to FIG. 15, the user may configure the reference image with different effects and the analysis area with the analysis function according to the constituted data in Table 4, including combination of the designated computing object and the computing rule and/or the combination of the designated processing object and the processing rule. When at least one of the constituted data of the reference image, the position rule, the synthesis parameter, the constituted data of the analysis area, the analysis mode, and the diagnosis rule is different, the analysis diagnosis configuration with different uses may be acquired. The analysis configuration with different uses and effects may be acquired via the switch configuration. The specified record information with different uses may be acquired via the record configuration.

In addition, when the constituted data is shown as FIG. 3, the user may configure the constituted data, the position rule, the synthesis parameter, the analysis mode, and the diagnosis rule, related to the reference image and the analysis area, via "diagnosis configuration CD3" or "switch CD4", thereby acquiring the diagnosis configuration with different uses.

When the setting operation is finished and the enter key is pressed, the control part 10 (the configuration part) allows the each set configuration to be related and stored in the flash memory 9 (such as, as a configuration file), which is used as the default configuration of the thermal imaging device 13, without setting during each time of use, and then returns to the standby photographing state. Although the embodiment of performing the configuration by the users is described, the invention is not limited thereto. When the thermal imaging device 13 leaves the factory, the configuration related to the respective processing may be set, without manual setting, or the configuration file may be loaded to the thermal imaging device 13 before photographing after the configuration is performed in an external computer. Otherwise, the user may perform the configuration of part contents mentioned above.

The overall function of the thermal imaging device 13 is described hereinbelow.

An acquiring part, such as the photographing part 1, is used for acquiring the thermal imaging data.

A reference image designating part (the control part 10) is used for designating the constituted data for acquiring the reference image reflecting the morphological characters of a photographed body. According to the constituted data stored in the storage medium, the constituted data of the reference image can be designated. For example, the reference image reflecting the morphological characters may be acquired by designating one morphological constituted data related to the reference image or multiple constituted data at least including one morphological constituted data from the "benchmark 1", "benchmark 2", and "auxiliary 1" stored in FIG. 4, by designating the morphological constituted data "benchmark 1 (processing)" represented by the processing object (the morphological constituted data, or the morphological constituted data and the auxiliary constituted data) combined with the specified processing rule, or by designating the auxiliary constituted data "benchmark 1 (computing)" represented by the computing object combined with the specified computing rule and one morphological constituted data. In addition, according to the thermal imaging data acquired via photographing, the constituted data of the reference image may be designated. In short, based on the constituted data stored in the storage medium, the constituted data for acquiring the reference image reflecting the morphological characters is designated. For example, the constituted data for acquiring the reference image may be selected from the constituted data stored in the storage medium. In addition, the morphological constituted data may be acquired by designating the processing object and the processing rule from the constituted data stored in the storage medium, or the reference image may be acquired according to the morphological constituted data and the auxiliary constituted data acquired by designating the computing object and the computing rule from the constituted data stored in the storage medium. Besides the prestored constituted data, the suitable constituted data may be acquired via processing or computing, or the suitable reference image may be acquired thereby.

The detailed designation way may be to select the default constituted data. The constituted data may be selected according to operation of users. For example, the constituted data may be selected according to the selection of the body selecting information by the users combined with the specified determined type of the constituted data, the constituted data may be selected according to the selection of the identity information of the constituted data by the users, or according to the operation of a specified key, the constituted data corresponding to the key may be selected. Otherwise, according to the specified triggering condition, the constituted data corresponding to the triggering condition may be determined.

A reference image position setting part (the control part 10) is used for setting the position parameter of the reference image reflecting the morphological characters acquired by the designated constituted data in an infrared thermal image. In the detailed position setting embodiment, the position parameter of the reference image may be automatically set according to a specified position rule. For example, according to the constituted data stored in the storage medium and the related position information, the position parameter of the reference image acquired by the constituted data represented by the position information in the infrared thermal image may set as the position parameter of the reference image acquired by the constituted data located in the infrared thermal image. Further, according to a specified self-adaptive area, the position parameter of the reference image located in the infrared thermal image may be automatically set. Further, a main object having the specified position relation with the reference image may be determined first and the position parameter of the main object located in the infrared thermal image may be set, and then according to the position parameter of the main object in the infrared thermal image and the specified position relation between the reference image and the main object, the position parameter of the reference image in the infrared thermal image may be set. According to the designated position default by the thermal imaging device 13, the position parameter of the reference image may be set.

In addition, according to operation (such as inputting the position parameter) of the users, the position parameter of the reference image may be set.

A display controlling part (the control part 10) is used for controlling the reference image with the specified dimension acquired by the designated constituted data to be displayed with the infrared thermal image generated by the thermal imaging data acquired by the photographing part together according to the specified position. There are multiple embodiments of displaying with the infrared thermal image.

When the reference image is one synthesis object, according to the specified position, it is continuously synthesized with the infrared thermal image generated by the thermal imaging data acquired by the photographing part, and then the synthesis image of the reference image and the infrared thermal image is displayed, thereby realizing the simultaneous display. In the embodiment, the synthesis may be performed according to a specified transparency ratio. The specified transparency ratio may be a fixed value, such as a default value stored in the thermal imaging device 13, a setting value set via the operation part 11 by the users, or the information related to the transparency ratio in the attribute of the constituted data of the acquired synthesis object. The transparency ratio of the synthesis object represents a ratio of the synthesis object and the synthesis pixels acquired by the synthesis object and the background (such as the infrared thermal image) during synthesis. For example, when one synthesis object is synthesized with the background, according to "image data of synthesis object×transparency ratio of synthesis object+image data of background×(1−transparency ratio of synthesis object)", the image data of the synthesized pixels is acquired. In addition, when the parameter of the transparency ratio is not set, the default transparency ratio is one.

In one embodiment, when there are several synthesis objects to be synthesized with the background (such as the infrared thermal image), according to the synthesis sequence and transparency ratio of each synthesis object, the synthesis objects are successively synthesized to acquire the final synthesis image. For example, when there are a synthesis object 1 (the synthesis sequence is one) and a synthesis object 2 (the synthesis sequence is two), the synthesis object 1 is first synthesized with the background according to the transparency ratio thereof to acquire medium data "image data of the synthesis object 1×the transparency ratio of the synthesis object 1+image data of the background×(1−the transparency ratio of the synthesis object 1)", and then the synthesis object 2 is synthesized with the medium data according to the transparency ratio thereof, that is, the acquired synthesis pixel is acquired according to the following formula: the synthesis object 2*the transparency ratio of the synthesis object 2+the medium data*(1−the transparency ratio of the synthesis object 2).

In one embodiment, according to the pixel position of the reference image in the infrared thermal image, the selective pseudo-color processing is performed for the thermal imaging data acquired by photographing to acquire the displayed image. In detail, the image data of the reference image at the superimposed pixel position may be as the image data of the superimposed image at the pixel position, the pseudo-color conversion is not performed for the thermal imaging data at the superimposed pixel position and is only performed for the thermal imaging data except the superimposed pixel position to acquire the image data of the infrared thermal image, thereby generating the displayed image, which may accelerate the processing speed in certain application. For the reference image of an edge contour, if this mode is used to process the reference image or the auxiliary object, corresponding identifying information may be first attached to the attribute of the constituted data. The pseudo-color processing performed for the thermal imaging data at the pixel position in the thermal imaging data to which the reference image corresponds is different from that for the thermal imaging data at other pixel positions, such as the pseudo-color processing of different pseudo-color plates or the pseudo-color processing after subtracting a specified value from the thermal imaging data at the pixel position in the thermal imaging data to which the reference image corresponds, to generate the synthesis image.

In one embodiment, for example, according to a threshold range (such as an AD value range) of the thermal imaging data acquired via photographing, the transparency ratio of the reference image synthesized with the thermal imaging data may be determined. In detail, the transparency ratio of the reference image synthesized with the infrared thermal image in the threshold range may be zero, and that outside of the threshold range may be one, thereby avoiding shading important parts (in the threshold range) of the infrared thermal image. In the embodiment, the specified transparency ratio may also be changeable values.

The display controlling part controls the display part 4 to display the reference image and the infrared thermal image, and controls to display image data of other specified information when the display interface is configured to further display other specified information. For example, in FIG. 8, the display image may include an image 802 of the reference image and the infrared thermal image and an image 801 of other specified information. Further, the analysis area may also be displayed, and preferably the analysis area may be displayed with the image of the morphological character as the reference in at least one of a color, a transparency ratio, or a line-type.

An analysis area determining part is used for determining the constituted data of the analysis area. Preferably, the analysis area determining part may determine the constituted data of the analysis area from the constituted data having the specified position relation with the constituted data of the reference image. For example, in FIG. 13, the analysis area may be acquired by designating one or more constituted data from the related "benchmark 1", "benchmark 2", and "auxiliary 1" with the specified position relation stored in the flash memory 9. The designated object is combined with the specified computing rule and/or processing rule, to acquire the constituted data of the analysis area. Preferably, the designated object may be the constituted data of the reference image or the constituted data of the object having the specified position relation with the reference image. In addition, the constituted data of the analysis area may be determined according to the constituted data with the specified position relation and the default position rule. For example, the constituted data of the analysis area may be determined from the constituted data (if there is no prestored specified position relation, the specified position relation may be defined by the default position rule of the thermal imaging device 13) related to the constituted data of the reference image. The specified position relation between the reference image and the analysis area may be acquired according to the information of the specified position relation stored in the storage medium in advance, may be set by users, or may be determined according to the default position rule of the thermal imaging device 13. In addition, the specified position relation between the constituted data acquired by computing and/or processing the designated object and the designated object or other object having the specified position relation with the designated object may be determined by a corresponding computing rule or processing rule.

The detailed determination way is to select the default constituted data. The constituted data may be selected according to operation of users. For example, the constituted data may be selected according to the selection of the body selecting information by the users combined with the specified determined type of the constituted data, the constituted data may be selected according to the selection of the identity information of the constituted data by the users, or according to the operation of a specified key, the constituted data corresponding to the key may be selected. Otherwise, according to the specified triggering condition, the constituted data corresponding to the triggering condition may be determined, thus to acquire the analysis area.

In addition, the constituted data of the analysis area may also be determined from the constituted data without the specified position relation. For example, the constituted data of the analysis area may be determined from the constituted data related to the constituted data of the reference image (there is no prestored specified position relation therebetween), and the position parameter therebetween may be set by users. In addition, the constituted data of the analysis area may also be determined according to the constituted data (such as points, lines, or planes) of the analysis area set by users. Due to the reference of the reference image, it is more convenient than the prior art.

An analysis area position setting part is used for setting the position parameter of the analysis area located in the infrared thermal image.

For example, the position parameter of the analysis area may be automatically set according to a specified position rule. For example, based on the constituted data and the related position information stored in the storage medium, the position parameter of the analysis area acquired by the constituted data represented by the position information in the infrared thermal image is set as the position parameter of the analysis area acquired by the constituted data in the infrared thermal image. Otherwise, according to a specified self-adaptive area, the position parameter of the analysis area located in the infrared thermal image may be automatically set. Otherwise, a main object having the specified position relation with the analysis area may be determined first and the position parameter of the main object in the infrared thermal image may be set, and then based on the specified position relation between the analysis area and the main object and the position parameter of the main object located in the infrared thermal image, the position parameter of the analysis area located in the infrared thermal image may be set. Otherwise, according to the designated position defaulted by the thermal imaging device 13, such as the default position parameter, the position parameter of the analysis area may be set.

In addition, according the operation (such as inputting the position parameter) of the users, the position parameter of the analysis area may be set.

The setting (the determination of the constituted data, the setting of the position parameter) of the analysis area and the reference image may have different sequences. For example, the analysis area position setting part may be used for setting the position parameter of the analysis area in the infrared thermal image, according to the position parameter of the reference image in the infrared thermal image set by the reference image position setting part and the specified position relation between the reference image and the analysis area. The reference image position setting part may be used for setting the specified position and specified dimension of the reference image in the infrared thermal image, according to the position parameter of the analysis area in the infrared thermal image set by the analysis area position setting part and the specified position relation between the reference image and the analysis area. Otherwise, the main object having the specified position relation with the analysis area and the reference image may be determined first and the position parameter of the main object located in the infrared thermal image may be set, and then based on the specified position relation between the above both and the main object and the position parameter of the main object in the infrared thermal image, the position parameters of the analysis area and the reference image in the infrared thermal image may be set.

According to the constituted data having the specified position relation with the constituted data of the reference image or the constituted data with the related relation, the analysis area is set, which is called the analysis area to which the reference image corresponds.

A thermal image analyzing part is used for analyzing the thermal imaging data (including the data acquired after specified processing for the thermal imaging data) acquired by the acquiring part (the photographing part 1) according to a specified analysis mode, based on the analysis area with the position parameter, to acquire an analysis result. Preferably, the specified analysis mode at least includes one or a combination of the followings:

1) the analysis mode acquired according to the analysis mode information related to the constituted data of the determined analysis area;

such as the analysis mode acquired according to the analysis mode information related and stored with the constituted data of the analysis area;

2) the analysis mode that is set according to the analysis mode information related to the position rule or position information of the position parameter of the acquired analysis area, thereby achieving the flexible analysis and facilitating the use when the analysis area is changed with different position parameters;

3) the analysis mode acquired according to the analysis mode information related to a corresponding computing and/or processing rule and/or the analysis mode information related to a designated object, when the constituted data of the analysis area is acquired by computing and/or processing the designated object. In certain conditions (for example, the area acquired after deformation of a contour may adopt the same analysis mode of the contour, such as computing the maximum temperature), the analysis mode information may correspond to the constituted data of the analysis area, thereby simplifying the operation.

In addition, the analysis mode may be a default mode of the thermal imaging device 13 or set by users. Obviously, there may be multiple analysis modes in the above.

In one embodiment, the temperature analysis is taken for example. Based on the control of the control part 10, the image processing part 2 performs specified processing, such as modification or interpolation, for the thermal imaging data acquired by the photographing part 1, and based on the position parameter of the analysis area in the infrared thermal image, extracts the thermal imaging data determined by the set analysis area, performs temperature conversion to acquire the temperature values to which the thermal imaging data corresponds, and then analyzes the acquired temperature values according to the analysis mode. For example, when the analysis mode is to compute the maximum, the maximum temperature value may be extracted as the analysis result. When the analysis area includes a plurality of area units, such as the area units S01, S02 of the analysis area F1 in FIG. 6, the temperature conversion and analysis is performed for the thermal imaging data in each area unit one by one, to acquire the analysis result of each area unit, the computed analysis result is stored with the number of the area unit in a specified area of the temporary storage part 6, and then the interrelated analysis result is computed and acquired according to the relation of the units in the analysis mode and the analysis result of each area unit.

In addition, the temperature conversion of the thermal imaging data in the analysis area may be to convert all thermal imaging data in the analysis area to temperature values, to convert specified part thermal imaging data to the temperature values, or to decide the conversion of all thermal imaging data or the part thermal imaging data in the analysis area according to different analysis modes such as computing the maximum temperature, the minimum temperature, or the average temperature. For example, when the analysis mode is to compute the maximum temperature in the analysis area, with regard to the thermal imaging data in the analysis area, the AD values of the thermal imaging data are compared, the maximum AD value is converted to the temperature value, without converting all thermal imaging data in the analysis area to the temperature values. In addition, there are conditions including different algorithms. For example, when the maximum temperature is computed, according to the average value of AD values of a specified number of adjacent pixels instead of the single pixel, the AD value of the adjacent pixel with the maximum average is converted to the temperature value, and the average of the temperature values of the thermal imaging data of the adjacent pixel is as the maximum temperature value. The thermal imaging data is converted to the temperature value after specified processing. In one embodiment, according to the radiation coefficient, environment temperature, humidity of the set photographed body, the distance between the photographed body and the thermal imaging device 13, and conversion coefficient between the AD values of the thermal imaging data and the temperature, the temperature values are acquired via the specified conversion formula. In addition, the thermal imaging data determined by the analysis area, as shown in FIG. 6, may be the thermal imaging data in the analysis units S01, S02, the thermal imaging data outside of the analysis units S01, S02, or the thermal imaging data of the pixels where the lines of the analysis units S01, S02 are. The attribute of the constituted data of the analysis area may be determined in advance.

In addition, the thermal image analysis is not limited to convert the thermal imaging data to temperature values, and the analysis may be to convert the thermal imaging data to radiation energy values, gray-scale values, or radiation ratio values. Obviously, the analysis for the acquired thermal imaging data is not limited to the single-frame thermal imaging data, and the analysis may also be performed for the multi-frame thermal imaging data stored in the temporary storage part 6 or one-frame thermal imaging data acquired after integral calculation for the multi-frame thermal imaging data.

A diagnosing part is used for diagnosing according to a specified diagnosis rule to acquire a diagnosis result according to the analysis result acquired by the thermal image analyzing part. Preferably, the diagnosis rule at least includes the diagnosis rule set according to the diagnosis rule related to the analysis mode in advance, such as the analysis mode and the related diagnosis rule acquired according to the information of the diagnosis rule related to the analysis mode information.

Figure 16:
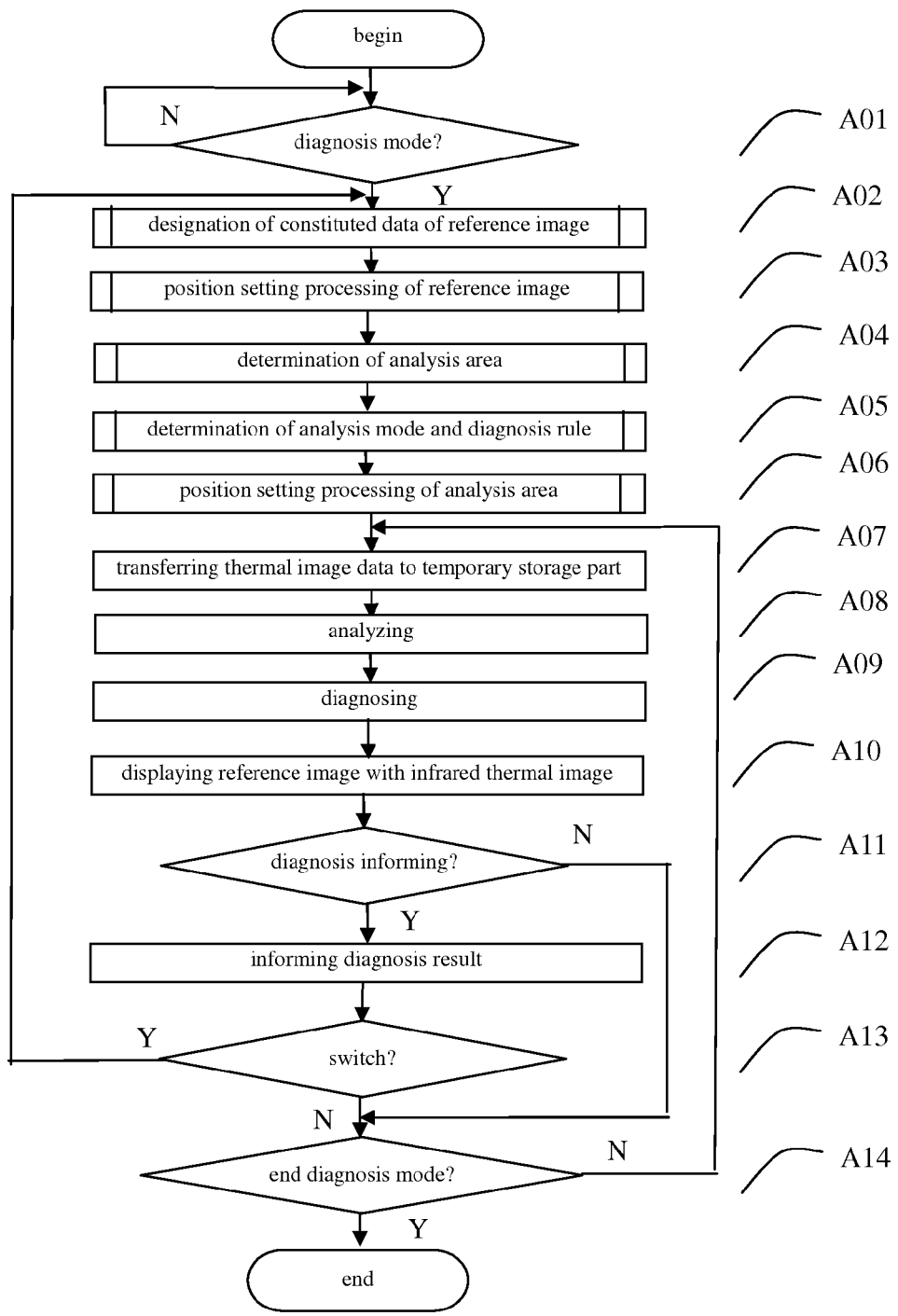
FIG. 16 is a flow chart showing a diagnosis mode.
Figure 17:
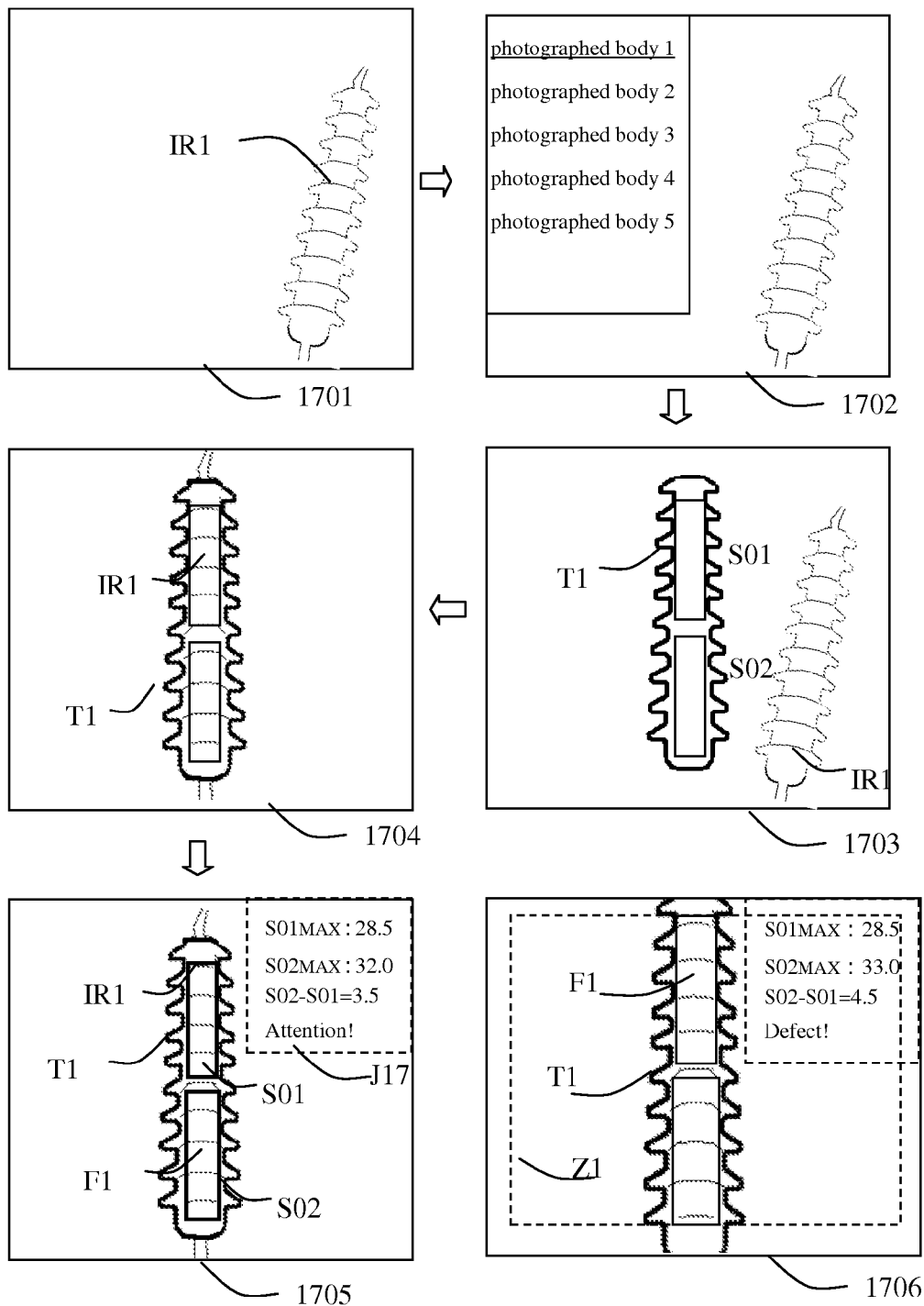
FIG. 17 is a schematic diagram showing display interfaces in the process of photographing a photographed body 1 via the reference image and the diagnosing process.

Referring to the flow chart in FIG. 16, the control steps in the first embodiment are described. FIG. 17 is a schematic diagram showing display interfaces during a photographing, analyzing, and diagnosing process for a photographed body 1 via the reference image composed of T1 and F1. In the embodiment, the user may press the mode key of the operation part 11 to enter into a diagnosis mode, and can examine the analysis diagnosis result when pressing the analysis key.

In step A01, the control part 10 continuously monitors if a user selects a diagnosis mode. In a standby photographing state, the display part 4 displays the dynamic infrared thermal image. According to the photographing angle and distance at that moment, the infrared thermal image in 1701 in FIG. 17 is acquired. As for a thermal image IR1 of the photographed body 1, in the prior art, the photographing distance and parts of the photographed body 1 and the settings of the analysis area, the analysis mode, and the diagnosis rule may confuse the user. To ensure the photographing correction of the photographed body 1, the setting convenience of the analysis area, the analysis mode and the diagnosis rule, and the correction of the analysis and diagnosis via the reference of the reference image, the user selects the diagnosis mode via the operation part 11 and performs step A02.

Figure 18:
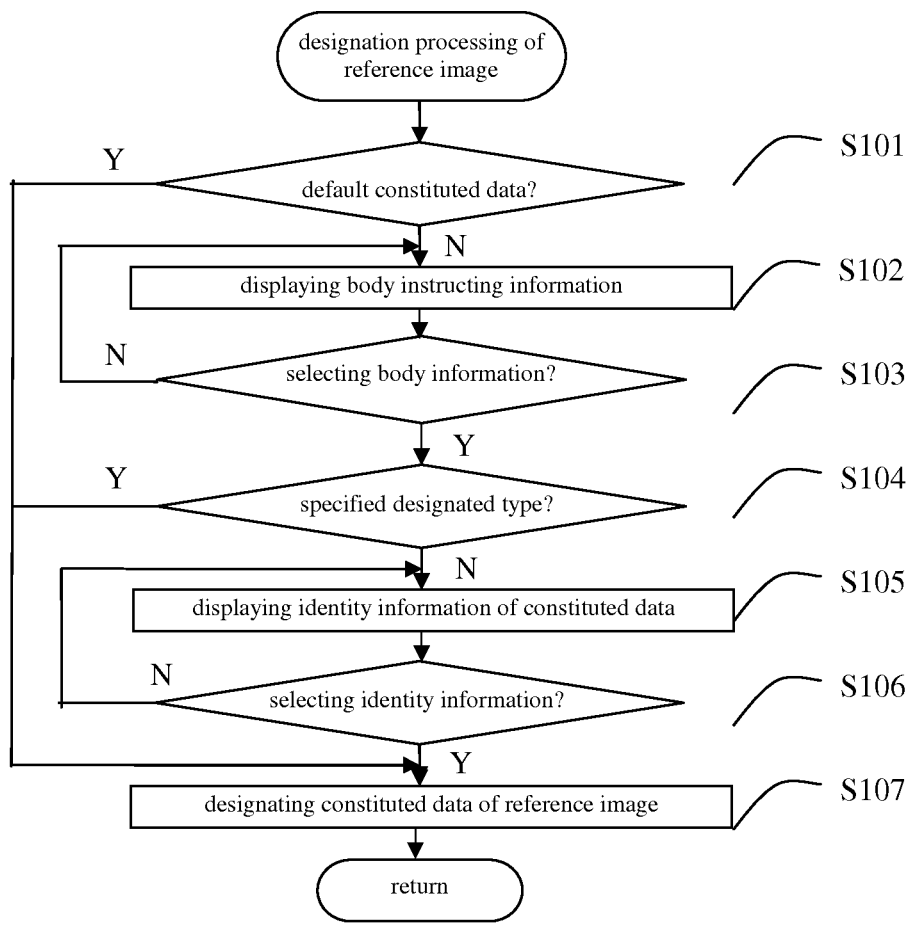
FIG. 18 is a flow chart showing designation processing of constituted data of a reference image.

In step A02, the control part 10 performs designation of the constituted data of the reference image, as shown in steps S101-S107 in FIG. 18.

Figure 19:
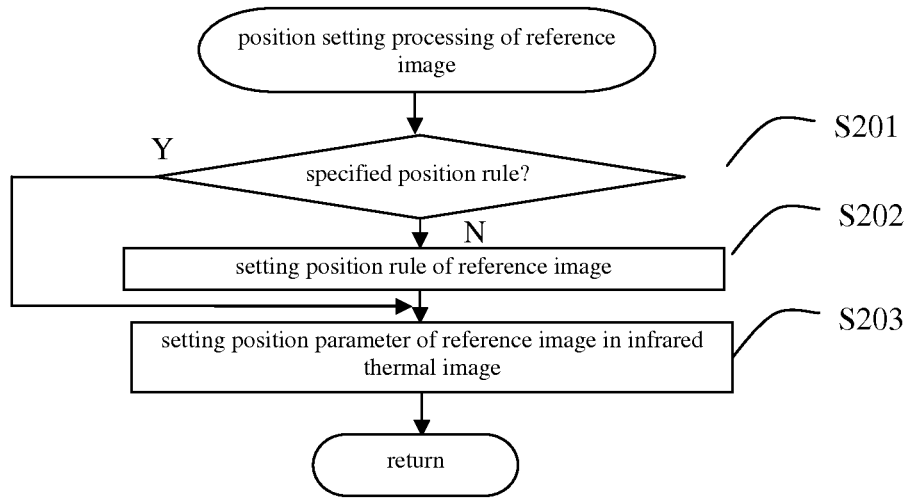
FIG. 19 is a flow chart showing setting processing of a position of the reference image.

In step A03, the control part 10 performs setting processing of the position parameter of the reference image in the infrared thermal image, as shown in steps S201-S203 in FIG. 19.

Figure 20:
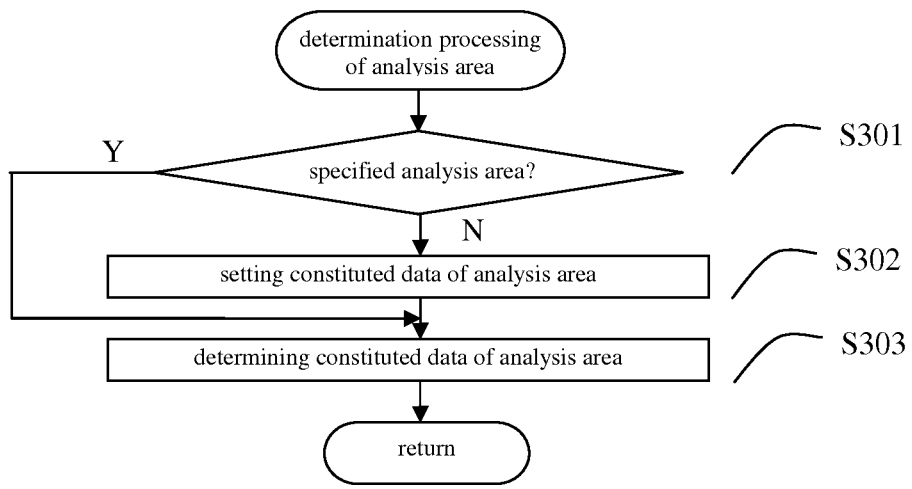
FIG. 20 is a flow chart showing determination processing of constituted data of an analysis area.

In step A04, the control part 10 performs determination of the constituted data of the analysis area, as shown in steps S301-S303 in FIG. 20.

Figure 21:
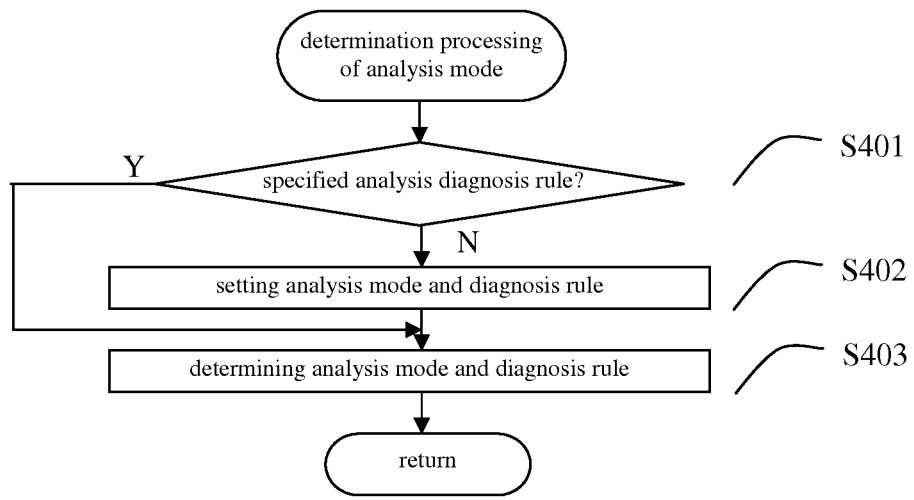
FIG. 21 is a flow chart showing determination processing of the analysis mode and the diagnosis rule.

In step A05, the control part 10 performs determination processing of the analysis mode to which the analysis area corresponds and the diagnosis rule to which the analysis mode corresponds, as shown in steps S401-S403 in FIG. 21.

Figure 22:
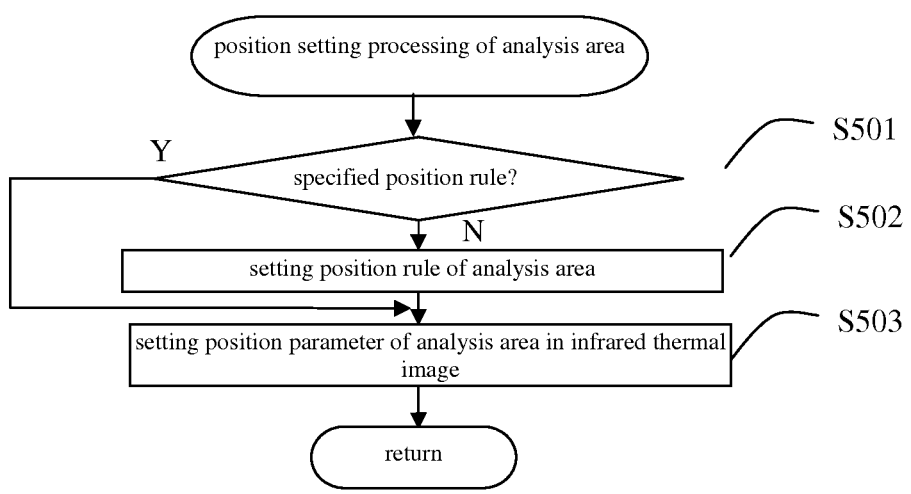
FIG. 22 is a flow chart showing setting processing of the position of the analysis area.

In step A06, the control part 10 performs setting processing of the position parameter of the analysis area in the infrared thermal image, as shown in steps S501-S503 in FIG. 22.

In step A07, the thermal imaging data is acquired, and the thermal imaging data acquired via photographing is transferred to the temporary storage part 6.

In step A08, the analysis is performed. Based on the set analysis area F1, according to the specified analysis mode, the thermal imaging data acquired by the photographing part 1 is analyzed, to acquire an analysis result. For example, the image processing part 2 may convert the thermal imaging data (the thermal imaging data in S01, S02) determined by the analysis area F1 (S01, S02) to temperature values, and may compute according to the analysis mode acquired by the analysis mode information of F1 related to the analysis area F1. The computed analysis result data, such as the maximum temperature of the area units S01, S02 and the temperature difference between S01 and S02, is stored to a specified area of the temporary storage part 6.

In step A09, the diagnosis is performed. In detail, for example, the control part 10 (as the diagnosing part) may compare the analysis result acquired by analysis and the diagnosis threshold in the diagnosis rule corresponding to the analysis mode according to a comparing relation in the diagnosis rule, to acquire a diagnosis result.

In step A10, the reference image acquired by the determined constituted data based on the specified dimension set by the position setting part is displayed with the infrared thermal image according to a specified position. In detail, in the embodiment, the constituted data is the constituted data of T1 and the constituted data of F1. The reference image (T1 and F1) acquired after specified processing (such as scaling) is synthesized with the infrared thermal image according to the specified position, and the synthesized image data is stored in the temporary storage part 6. Then, the control part 10 controls the reference image and the infrared thermal image to be displayed on the display part 4. As shown in a display interface 1703, there is the greater difference between the thermal image IR1 of the photographed body and the contour image T1. If there is no reference image reflecting the morphological characters of the photographed body, the user fails to hold the shape of the thermal image IR1 of the photographed body, the imaging position, dimension, and angle in the infrared thermal image, thereby omitting focused measuring parts and causing complicated setting operation of the analysis area. Further, if there is no shape reference of T1, the reference effect of F1 is weak.

In step A11, the control part 10 detects if a diagnosis informing instruction is received. If no, enter into step A14 and determine if the diagnosis mode is exited. If no, return to step A07, and in the steps A08, A09, the newly acquired thermal imaging data is analyzed, and the analysis result and diagnosis result replace the analysis result and diagnosis result stored before and are stored in the specified area of the temporary storage part 6. Then, in the step A10, the reference image is displayed with the infrared thermal image acquired by the photographed thermal imaging data, reflecting a continuous display state of the dynamic infrared thermal image continuously acquired and the reference image.

According to the visual reference of the contour image T1, the user can understand the shape requirement of the thermal image IR1 of the photographed body to be photographed, the imaging position, dimension, and angle in the infrared thermal image, and then adjust the photographing distance, angle, and imaging position between the optical part of the thermal imaging device 13 and the photographed body 1, to achieve a superimposed state of the thermal image IR1 of the photographed body and the contour image T1 visually in FIG. 17 (a display interface 1704). At this moment, the user presses the analysis key to enter step A12.

In the step A12, the analysis result and the diagnosis result are displayed. As shown in a display interface 1705 in FIG. 17, the analysis result and diagnosis result J17 stored in the specified area are displayed on the display part 4, and the user can make judgment according to the displayed analysis result and diagnosis result. In addition, the analysis result and diagnosis result may not be displayed. For example, the analysis result and diagnosis result for controlling other devices may be output from the communication interface I/F 5. In the display interfaces 1703 and 1704 in FIG. 17, the analysis area F1 is configured to be displayed, and it may be configured to be not displayed.

In step A13, if the switch key is pressed is determined.

If pressed, perform the corresponding switch, and return to the step A02. According to the switch configuration, the constituted data of T1 and F1 is determined to acquire the reference image, the analysis area F1 is as a main object, the position parameter of the analysis area F1 in the infrared thermal image is first set, and then according to the position and dimension of the analysis area F1, the specified position and specified dimension of the reference image (including T1 and F1) in the infrared thermal image are set. The thermal image of the photographed body that is photographed according to the reference image is shown in a display interface 1706 in FIG. 17, and due to the difference of the photographing distances, the analysis and diagnosis result shown in the display interface 1706 is different from that in 1705, and the temperature different increases to 4.5 (defect). Thereby, the user can make overall judgment according to the analysis and diagnosis result.

The display effect of the analysis area F1 as the main object represents that the analysis part represented by the analysis area F1 is displayed in a self-adaptive area Z1 at the maximum. The part of the contour T1 is overflowed, which meets the applied demand and is acceptable. According to the different measuring aims, different main objects may be set to represent the focused area to be observed. The position parameter of the main object in the infrared thermal image may be used for configuring the position parameter of the reference image or the analysis area in the infrared thermal image, which is convenient and flexible.

In addition, the switch is not limited to the change of the position rule. The switch may be performed for the reference image, the analysis area, the synthesis parameter, the analysis mode, the diagnosis rule, or a combination thereof, thereby achieving different measuring or observing effects. The switch is one preferred embodiment, and the switch step A13 may not be performed.

In step A14, if the diagnosis mode is exited is determined. If no, return to the step A07. If a user does not release the analysis key, in the step A12, the analysis and diagnosis result in real time acquired by analysis and diagnosis processing for the thermal imaging data acquired in the step A07 is displayed, and if the user releases the analysis key, the dynamic infrared thermal image and the reference image are displayed.

Referring to FIG. 18, the designation of the constituted data of the reference image is described.

In step S101, if there is default constituted data is determined. If yes, jump to step S107. The control part 10 selects the default constituted data. If no, perform step S102.

In step S102, based on Table 4 stored in the flash memory 9, the control part 10 (a body information selecting part) allows the display part 4 to display a specified number of the body selecting information at the specified position, such as a body selecting information list LB as shown in the display interface 1702 in FIG. 17.

In step S103, then according to the cognition of the photographed body 1 at the photographing scene, such as an equipment indicator at the scene, the "photographed body 1" displayed on the display part 4 is selected via the operation part 11. The control part 10 is used for selecting the body information according to the selection of the body selecting information.

In addition, when the body information in Table 4 is composed of attribute information of multiple attributes, the body information is finally selected via display and the multiple selections for the attribute information (the body selecting information) of multiple attributes of the body information. For example, supposing that "photographed body 1" is composed of the attribute information "substation 1", "equipment area 1", and "equipment 1" corresponding to the substation attribute, the equipment area attribute, and the equipment type attribute, respectively, the selection operation is to select "substation 1" from a specified number of the body selecting information (the attribute information) corresponding to the displayed substation attribute, to select "equipment area 1" from a specified number of the body selecting information (the attribute information) corresponding to the equipment area attribute, and then to select "equipment 1" from a specified number of the body selecting information (the attribute information) corresponding to the equipment type attribute, thus to finally select "photographed body 1". The selection operation may be divided into the multiple selection of the attribute information to finally select the body information.

In step S104, the control part 10 determines if there is the constituted data (such as, only one constituted data is related) of a specified designated type in the constituted data related to the body information corresponding to the selected body selecting information.

If only one constituted data is related, the control part 10 may select the constituted data according to the body information to which the body selecting information selected by the users corresponds. For example, when the flash memory 9 stores the body information and the related constituted data as shown in FIG. 3, in step S107, the control part 10 determines the constituted data of T1 as the constituted data of the reference image.

When the flash memory 9 stores the body information and the related multiple types of the constituted data as shown in FIG. 4, in the embodiment, since the specified designated type of the constituted data is set in advance, the step S107 is performed, the control part 10 designates "constituted data of T1" and "constituted data of F1" as the constituted data according to "photographed body 1" and the specified designated type "benchmark 1" and "auxiliary 1". If no, that is, the body information selected in the step S103 is related to the constituted data of multiple types and the specified designated type is not set in advance, step S105 is performed.

In step S105, the control part 10 allows the display part 4 to display identity information of the respective constituted data for users to select. The identity information may be a file name, a number, or a thumbnail representing the identity indicator of the corresponding constituted data. For example, the thumbnail corresponding to the constituted data may be displayed for the users to select, and one or more therein may be selected.

In step S106, when the users perform selection, the step S107 is performed.

In step S107, the reference image designating part is used for designating the constituted data for acquiring the reference image. Then, the constituted data of T1, F1 read from the flash memory 9 and the specified position relation therebetween is transferred to the temporary storage part 6.

In the above embodiment, the constituted data designated by the reference image designating part may be the default constituted data, may be designated according to the constituted data related to the selected body information, or may be the constituted data satisfying the specified designated type automatically determined according to the specified designated type based on the constituted data stored in the storage medium. The way of designating the constituted data of the reference image according to the constituted data related to the body information may be to select the constituted data for acquiring the reference image from the constituted data related to the body information, or to designate the processed constituted data as the constituted data for acquiring the reference image after designating a processing object from the constituted data related to the body information. Otherwise, the constituted data may be designated, as the user selects the identity information of the constituted data. In addition, when the constituted data in the storage medium is not related to the body information, the steps S102, S103 are omitted, and the constituted data is selected according to the identity information of the constituted data. Further, the body information selecting step of the steps S102, S103 may be as one step before the determining step of the constituted data of the reference image, and is not limited in the determining step of the constituted data of the reference image. In addition, according to the operation of a specified key, the constituted data corresponding to the key is selected, and the constituted data corresponding to the triggering condition is determined based on the specified triggering condition.

Referring to FIG. 19, the setting processing of the position parameter of the reference image in the infrared thermal image is described.

In step S201, the control part 10 determines if there is a specified position rule. If yes, jump to step S203. If no, perform step S202.

In step S202, as the setting menu as shown in FIG. 9 and the corresponding prompt are displayed, the user is required to set the position rule. When finished, the position rule is record to the flash memory 9 as the subsequent default configuration.

In step S203, the position parameter of the reference image in the infrared thermal image is set.

In the embodiment, according to the preset position rule, that is, the type of the main object is "benchmark 1", the self-adaption is performed for computing the position parameter of the contour T1 in the infrared thermal image according to a centered position of the self-adaptive area Z1, and then the position parameter of F1 in the infrared thermal image is determined according to the specified position relation between F1 of the reference image (including the contour T2 and F1) and the contour T1. For example, according to the specified position relation therebetween and the position parameter of the contour T1 in the infrared thermal image, the scaling base point (such as a center point) of the contour T1 is used as the scaling base point of F1, F1 is scaled at the same scaling ratio of T1 to acquire the position parameter in the infrared thermal image. In the above position setting mode, the user is not necessary to perform manual operation to input the position parameter of the reference image, and during photographing, the thermal imaging device 13 may automatically set the specified position and the specified dimension of the reference image in the infrared thermal image according to the specified position rule, thereby ensuring the standards of the dimension and position of the thermal image of the photographed body and simplifying the operation.

Referring to FIG. 20, the determination of the constituted data of the analysis area is described.

In step S301, if there is a specified designated type of the constituted data of the analysis area is determined. If yes, step S303 is performed, and the control part 10 determines the constituted data of the analysis area according to the specified designated type. If no, step S302 is performed.

In step S302, the constituted data of the analysis area is configured. A setting menu as shown in FIG. 9 is used for configuring the constituted data of the analysis area, displaying the corresponding prompt or the setting bar of points, lines, and planes, which is provided for the users to set or select the type of the constituted data of the analysis area.

In step S303, the constituted data of the analysis area is determined.

In the embodiment, since the user selects the photographed body 1 and sets the specified designated type of the constituted data of the analysis area to be "auxiliary 1", the "constituted data of F1" is determined as the constituted data of the analysis area.

The constituted data of the analysis area may be the default constituted data, may be automatically determined according to the specified designated type of the constituted data combined with the selected body information, may be determined according to the selection of the identity information of the constituted data by the users, or may be the constituted data of the analysis area corresponding to the key according to operation for the specified key. Based on the specified triggering condition, the constituted data of the analysis area corresponding to the triggering condition may be determined, to acquire the analysis area. The way of determining the constituted data of the analysis area based on the constituted data related to the body information may be to select the constituted data for acquiring the analysis area from the constituted data related to the body information or to designate an object from the constituted data related to the body information and to designate the constituted data acquired by processing and/or computing as the constituted data for acquiring the analysis area.

Referring to FIG. 21, the determination processing of the analysis mode and the diagnosis rule is described.

In step S401, if there are a specified analysis mode and a diagnosis rule is determined. If yes, step S403 is performed, and the control part 10 determines the specified analysis mode and the diagnosis rule. If no, perform step S402.

In step S402, the setting menu as shown in FIG. 13 is displayed, and the user is required to set the analysis mode and the diagnosis rule. When the analysis mode and the diagnosis rule to which the analysis area corresponds are set, they are related and stored in the temporary storage part 6, and the analysis mode to which the newly set analysis area corresponds and the diagnosis rule to which the analysis mode corresponds are related and stored with the body information in the flash memory 9, such as storing in Table 4, for subsequent use. In addition, other analysis modes and the corresponding diagnosis rule prestored in the thermal imaging device 13 may be displayed for selection.

In step S403, in the embodiment, since the adoption of "analysis diagnosis 1" is configured beforehand, the analysis mode 1 (mode information of F1) related to the constituted data of F1 and the diagnosis rule 1 (diagnosis rule of F1) related to the analysis mode 1 are determined.

The analysis mode related to the analysis area F1 and the diagnosis rule related to the analysis mode are used, thereby avoiding trouble of the setting operation on the scene by users. Further, when there are multiple combinations of the analysis mode and the diagnosis rule related with each other, multiple complicated calculations may be performed. In addition, the analysis mode corresponding to the analysis area and the diagnosis rule corresponding to the analysis mode may not be related and stored with the constituted data of the analysis area in advance, and they may be acquired according to other predetermined analysis mode and diagnosis rule or may be temporarily set in response to the setting operation of the users. The analysis mode corresponding to the analysis area and the diagnosis rule corresponding to the analysis mode may be related and stored with the constituted data of the analysis area in advance, may be other analysis mode and diagnosis rule in the thermal imaging device 13, or may be the analysis mode and diagnosis rule temporarily set by the users.

Referring to FIG. 22, the setting processing of the position parameter of the analysis area in the infrared thermal image is described.

In step S501, the control part 10 determines if there is a specified position rule. If yes, perform step S503. If no, perform step S502.

In step S502, the setting menu as shown in FIG. 9 is displayed, and the user is required to set the position rule of the analysis area. After finished, the determined position rule of the analysis area of this type is record to the flash memory 9, as the subsequent default configuration.

In step S503, the position parameter of the analysis area in the infrared thermal image is set. In the embodiment, the position rule of the analysis area is that the type of the main object is benchmark 1, the main object is self-adapted to compute the position parameter in the infrared thermal image according to a centered position of the self-adaptive area Z1, and then the position parameter of the analysis area F1 in the infrared thermal image is determined according to the specified position relation between the analysis area F1 and the contour T1. In a switch state, the type of the main object is auxiliary 1, the main object (the analysis area F1) is self-adapted to compute the position parameter in the infrared thermal image according to the centered position of the self-adaptive area Z1, and then the position parameter of the contour T1 in the infrared thermal image is determined according to the specified position relation between the analysis area F1 and the contour T1.

In addition, the main object may be acquired by the constituted data except the reference image and the analysis area. That is, the respective position parameter of the analysis area and the reference image is set according to the main object.

During photographing, according to the specified position rule, the position parameters of the reference image and the analysis area in the infrared thermal image are automatically set, and the user is not necessary to input the position parameter of the analysis area by manual operation, thereby ensuring standards of the dimension and position of the thermal image of the photographed body and simplifying the operation. It is not limited thereto. The control part 10 may determine the position parameters of the reference image and the analysis area in the infrared thermal image according to the position parameter inputted by the users via the operation part.

In addition, the designation of the constituted data of the reference image (the step A02), the position setting of the reference image (the step A03), the determination of the constituted data of the analysis area (the step A04), the position setting of the analysis area (the step A06), and the determination of the analysis mode and the diagnosis rule (the step A05) is described according to a certain step sequence, which may be in different sequence of priority according to different embodiments and may not be limited to the processing sequence described in this embodiment.

In addition, in the first embodiment, the analysis and diagnosis is always performed, the analysis and diagnosis result is continuously renewed, and the analysis and diagnosis result is displayed when the diagnosis informing instruction from the users is received. However, it may also be configured that the analysis and diagnosis is performed when the analysis key is pressed, the analysis and diagnosis result may be always displayed and refreshed, or the diagnosis result may be only displayed and the analysis result may not be displayed.

In addition, as shown in the display interface 1703, the position parameter of the reference image may be adjusted to match the thermal image IR1 of the photographed body in the infrared thermal image. Preferably, according to the adjustment of the users, the reference image position setting part and the analysis area position setting part change at least one of the position, dimension, and the rotating angle of the reference image and the analysis area in the infrared thermal image to remain the specified position relation therebetween unchanged. For example, when one of them is adjusted, the other one has the same change according to the adjusted position, dimension, or rotating angle, to remain the specified position relation therebetween unchanged.

According to the above, in the first embodiment, the constituted data of the reference image and the analysis area is designated according to the selection of the body information, thereby facilitating selection of the reference image and the analysis area corresponding to the photographed body. The reference image reflecting the predetermined morphological characters of the photographed body is displayed in the infrared thermal image, thereby facilitating to acquire the standard infrared thermal image. The constituted data of the reference image and the analysis area is designated from the constituted data with the specified position relation, to allow the set analysis area to be standard and to have the corresponding position with the reference image, thereby allowing the infrared thermal image and the analysis area acquired according to the reference image to be accurate with simple operation. The thermal image of the photographed body may be analyzed and diagnosed according to the analysis mode related to the analysis area and the diagnosis rule related to the analysis mode, thereby solving the setting problem of the analysis mode and the diagnosis rule, achieving the simple operation, reducing the skill requirements of the users, improving the photographing speed, being convenient for complicated analysis and diagnosis, and without omitting the photographed body. Thereby, the common users can achieve the better photographing level.

Embodiment Two

In the second embodiment, a thermal imaging device having the same structure with the thermal imaging device 13 in the first embodiment is provided, the flash memory 9 stores the diagnosis control program which is different from that in the first embodiment, and in response to a diagnosis instruction of the users, the thermal imaging data that is frozen and displayed, is analyzed and diagnosed. Further, the flash memory 9 stores the content as shown in FIG. 4 and the configuration as shown in FIG. 13.

Figure 23:
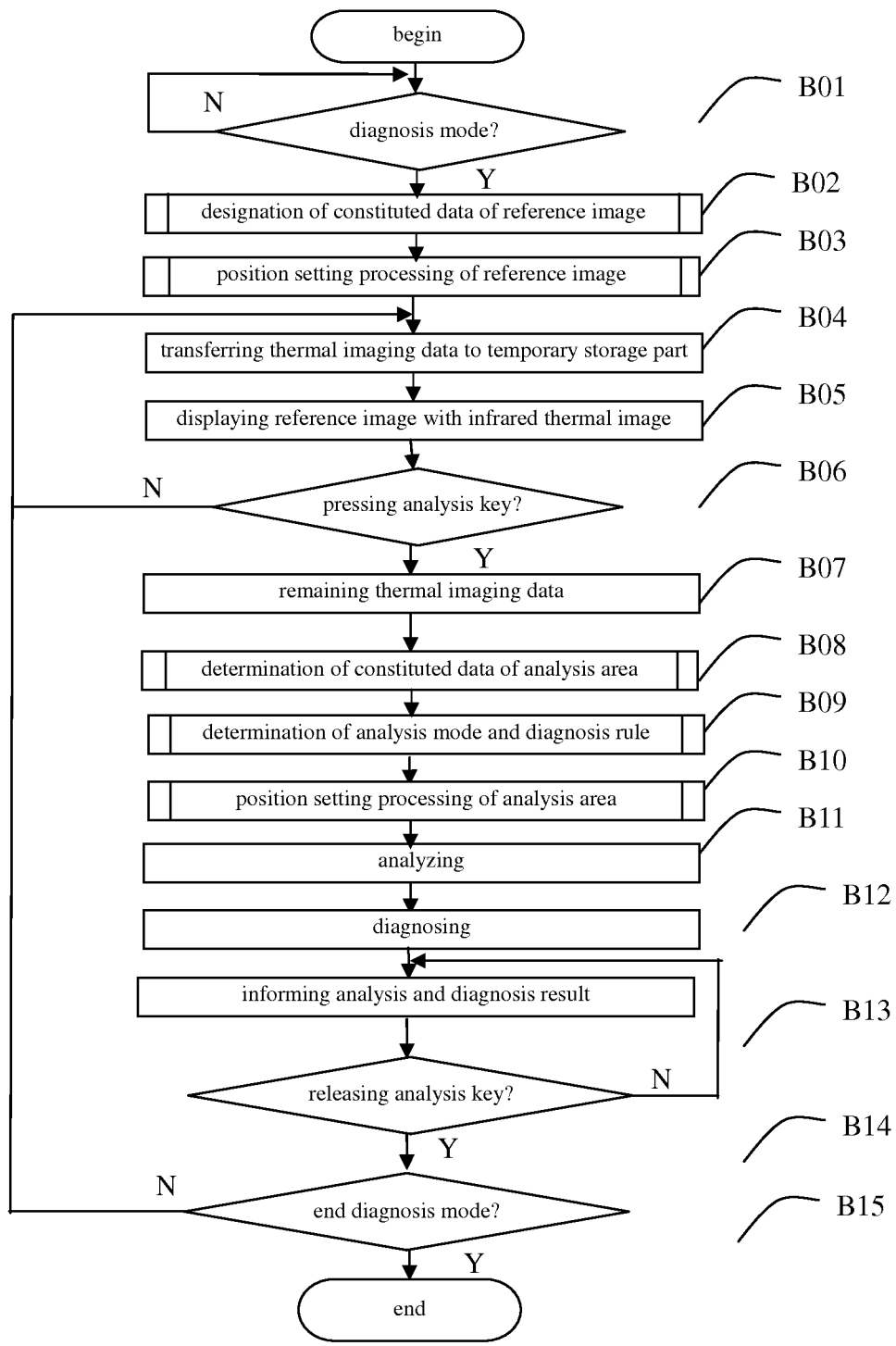
FIG. 23 is a flow chart showing a diagnosis mode according to a second embodiment.

Referring to FIG. 23, a control flow is described.

In step B01, the control part 10 continuously monitors if a diagnosis mode is selected. If yes, step B02 is performed.

In step B02, the control part 10 performs determination of the constituted data of the reference image, as shown in the steps S101-S107 in FIG. 18.

In step B03, the control part 10 performs setting processing of the position parameter of the reference image in the infrared thermal image, as shown in the steps S201-S203 in FIG. 19.

In step B04, then, the thermal imaging data acquired via photographing is transferred to the temporary storage part 6.

In step B05, the reference image acquired by the designated constituted data according to the specified dimension set by the position setting part is displayed with the infrared thermal image together according to the specified position, as shown in the display interface 1703.

In step B06, if a user presses the analysis key is determined. If no, return to the steps B04-B05. That is, the image formed by continuous synthesis of the reference image and the infrared thermal image acquired via photographing is displayed. When the user allows the thermal image IR1 of the photographed body and the contour T1 to be in the visual superimposed and matching state as shown in FIG. 17 (the display interface 1704) by adjusting the photographing distance, angle, and image position between the optical part of the thermal imaging device 13 and the photographed body 1, the user presses the analysis key to perform the next step.

In step B07, in response to the operation, the thermal imaging data acquired in the step B04 maintains in the specified area of the temporary storage part 6, or the synthesis image acquired in the step B05 or the infrared thermal image maintains in the specified area of the temporary storage part 6, and the synthesis image (or the infrared thermal image) is frozen.

In step B08, the control part 10 performs determination of the constituted data of the analysis area, as shown in the steps S301-S303 in FIG. 20.

In step B09, the control part 10 performs determination processing of the analysis mode to which the analysis area corresponds and the diagnosis rule to which the analysis mode corresponds, as shown in the steps S401-S403 in FIG. 21.

In step B10, the control part 10 performs setting processing of the position parameter of the analysis area in the infrared thermal image, as shown in the steps S501-S503 in FIG. 22.

In step B11, the analysis is performed for the remained thermal imaging data, and the acquired analysis result data, such as the maximum temperature of the area units S01, S02 and the temperature difference between S01 and S02, is stored to the specified area of the temporary storage part 6.

In step B12, the diagnosis is performed, and then the diagnosing part compares the analysis result data and a threshold to acquire a diagnosis result.

In step B13, the diagnosis result is informed. In the embodiment, the analysis and diagnosis result J17 is displayed on the display part 4, as shown in the display interface 1704. The user may make a judgment according to the analysis and diagnosis result. In addition, they may not be displayed. For example, the analysis and diagnosis result data provided for other devices may be output from the communication I/F 5, or the diagnosis result may be informed only.

In step B14, if the analysis key is released is determined. If yes, perform step B15, and if no, return to the step B13 and continuously display the analysis and diagnosis result.

In step B15, if the diagnosis mode is exited is determined. If no, return to the step B04, and if yes, exit.

According to the above, in the second embodiment, the user allows the infrared thermal image or the synthesis image to be frozen and displayed, in the visual matching state of the reference image and the infrared thermal image, to display the analysis and diagnosis result, which is different from the first embodiment, thereby ensuring the correction of the analysis. Thus, the analysis and diagnosis during infrared photographing is convenient, the skill requirement of the users is reduced, the photographing speed is improved, the difficulty of the diagnosis is reduced, and the operation is simple.

Embodiment Three

In the third embodiment, a thermal imaging device has the same structure with the thermal imaging device 13 in the first embodiment, and the flash memory 9 stores the content as shown in FIG. 3 beforehand.

Figure 24:
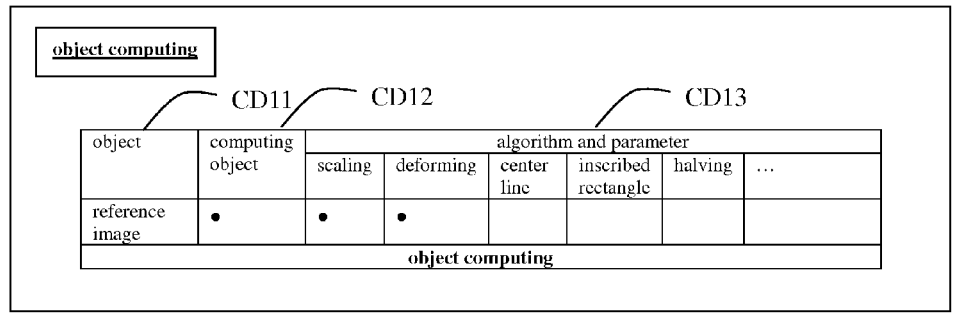
FIG. 24 is a schematic diagram showing a menu setting interface of object computing according to a third embodiment.
Figure 25:
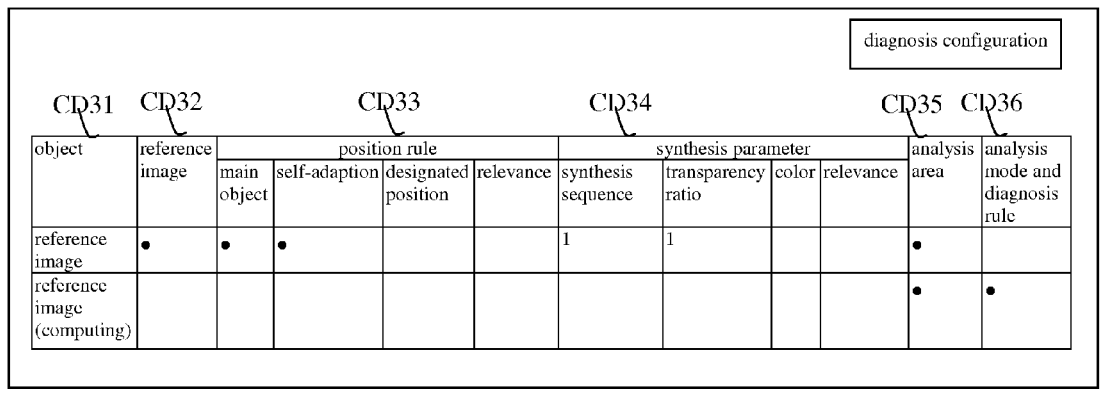
FIG. 25 is a schematic diagram showing a menu setting interface of the reference image, the analysis area, the analysis mode, and the diagnosis rule according to the third embodiment.
Figure 26:
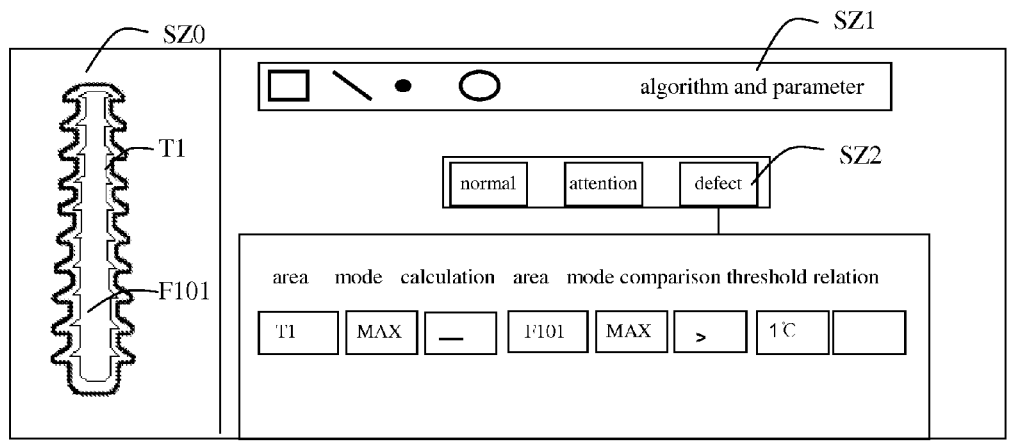
FIG. 26 is a schematic diagram showing another menu setting interface of the analysis mode and the diagnosis rule to which the analysis area corresponds according to the third embodiment.

To analyze the thermal field distribution of the specified area in the main part of the photographed body, such as a contour edge of the photographed body, the configuration set via "computing object CD2" is shown in FIG. 24. The computing object is "benchmark 1", and the computing rule is scaling based on a center point for acquiring the analysis area F101 subsequently. The configuration of "diagnosis configuration CD2" is shown in FIG. 25. Further, as shown in FIG. 26, the configuration of the analysis mode and the diagnosis rule is provided for the analysis area F101 acquired via computing and the T1 as the analysis area.

Figure 27:
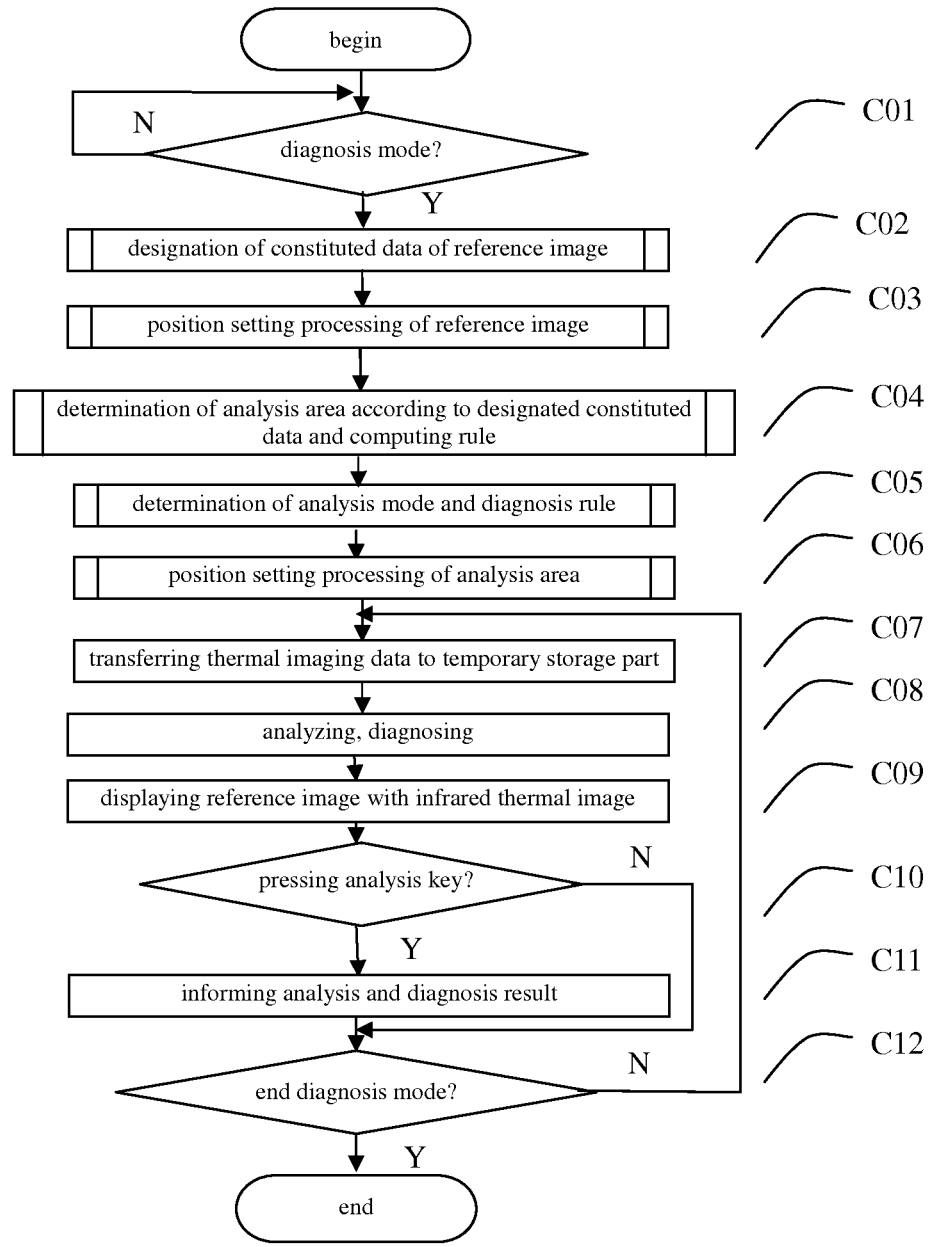
FIG. 27 is a flow chart showing a diagnosis mode according to the third embodiment.

According to the flow chart in FIG. 27, the control steps of the diagnosis mode in the third embodiment are described. FIG. 28 is a schematic diagram showing display interfaces during a photographing, analyzing, and diagnosing process for the photographed body 1 via the contour image T1 and the analysis area T1, F101. In the embodiment, the user presses the mode key of the operation part 11 to enter into the diagnosis mode, and when the analysis key is pressed, the analysis and diagnosis result may be examined.

In step C01, the control part 10 continuously monitors if a user selects a diagnosis mode. If yes, perform step C02.

In step C02, the control part 10 performs designation of the constituted data of the reference image. Based on Table 3 stored in the flash memory 9, a specified number of the body selecting information is displayed at the specified position of the display part 4. When the user selects "photographed body 1", the constituted data of T1 is designated.

In step C03, the control part 10 performs determination processing of the constituted data of the analysis area. In detail, according to the configuration in FIG. 24, the benchmark 1 is as the computing object (scaling and deforming based on a center point), and the constituted data (including the relative position relation with T1) of the analysis area F101 is related and stored with the number F101 of the corresponding analysis unit in the specified area of the temporary storage part 6. The area determined by T1 is also determined as the analysis area.

In step C04, the control part 10 performs determination processing of the analysis mode to which the analysis area T1, F10 corresponds and the diagnosis rule to which the analysis mode corresponds. In detail, according to the configuration in FIG. 26, the corresponding analysis mode and diagnosis rule are acquired.

In step C05, the control part 10 performs setting processing of the specified position and specified dimension of the reference image in the infrared thermal image. In detail, according to the specified position rule "self-adaptive area Z1, self-adaptively centered", the position parameter of the reference image T1 in the infrared thermal image is set.

In step C06, the control part 10 performs setting processing of the position parameter of the analysis area in the infrared thermal image. According to the position parameter of the reference image T1 in the infrared thermal image and the specified position relation between the analysis area and the reference image, the position parameter of the analysis area T1, F101 in the infrared thermal image is determined.

In step C07, then, the thermal imaging data acquired via photographing is transferred to the temporary storage part 6.

In step C08, the analysis and diagnosis is performed. That is, the thermal imaging data acquired by the photographing part is analyzed to acquire the analysis and diagnosis result, according to the specified analysis mode, based on the analysis area T1, F101 with the position parameter. The image processing part 2 converts the thermal imaging data (the thermal imaging data in T1, F101) determined by the analysis area T1, F101 to temperature values, computes according to the analysis mode to which the analysis mode corresponds, and then diagnoses according to the diagnosis rule. The computed analysis result data, such as the maximum temperature of the area units T1, F101, the temperature difference between T1 and F101, and the diagnosis result acquired by diagnosis, is stored to the specified area of the temporary storage part 6.

In step C09, the reference image T1 acquired by the determined constituted data according to the specified dimension set by the position setting part is displayed with the infrared thermal image together according to the specified position. As shown in the display interface 2802, there is greater difference between the thermal image IR1 of the photographed body and the reference image T1. If there is no reference of the reference image, the user fails to subjectively hold the shape of the thermal image IR1 of the photographed body, the imaging position, dimension, and angle in the infrared thermal image. Thus, the focused measuring parts may be omitted and the setting operation of the analysis area is complicated.

In step C10, the control part 10 detects if a diagnosis instruction is received. If no, step C12 is performed, to determine if the diagnosis mode is exited. If it is not exited, return to the step C07, and in the step C08, the acquired thermal imaging data is analyzed and diagnosed, and the analysis and diagnosis result is stored in the specified area of the temporary storage part 6, to replace the earlier analysis and diagnosis result. Then, in the step C09, the reference image is displayed with the infrared thermal image acquired by the thermal imaging data together. When the acquired thermal image IR1 of the photographed body and the reference image T1 as shown in FIG. 28 (a display interface 2803) achieve the visual superimposed matching state by adjusting the thermal imaging device 13, the user presses the analysis key to perform step C11.

In step C11, the analysis and diagnosis result is displayed. As shown in FIG. 28 (a display interface 2804), the analysis and diagnosis result J28 and the analysis area F101 stored in the specified area are displayed (the content capable of being displayed). The user makes the judgment according to the analysis and diagnosis result. However, the invention is not limited thereto. They may not be displayed. For example, the analysis data for controlling other devices may be output from the interface I/F 5. In the display interfaces 2802 and 2803 in FIG. 28, the analysis area F101 is not displayed, which may be configured to display.

In step C12, if the diagnosis mode is exited is determined. If no, return to the step C07. If the user does not release the analysis key, in the step C11, the analysis and diagnosis result in real time acquired after analyzing the thermal imaging data acquired in the step C07 is displayed. If the user releases the analysis key, the dynamic infrared image and the reference image are displayed.

According to the above, in the third embodiment, the analysis area is computed and acquired according to the reference image, thereby ensuring the convenience of the setting of the analysis area and accuracy of the subsequent analysis and diagnosis. The realization of the setting of the analysis area T1, F01 in the prior art is difficult. In the embodiment, the convenient setting of the analysis area, the analysis mode, and the diagnosis rule is achieved, the skill requirement of the users is reduced, the photographing speed is improved, and the operation is simple.

Embodiment Four

In this embodiment, a thermal imaging device having the same structure with the thermal imaging device 13 as shown in FIG. 1 stores control programs of record processing. The configuration of the specified record information is as shown in FIG. 29. Referring to FIG. 30, the flow chart of the embodiment is described.

In step D01, the control part 10 continuously monitors if a user selects a diagnosis mode. If yes, perform step D02.

The step D02 is similar to the steps A02-A12 in the first embodiment, the steps B02-B12 in the second embodiment, or the steps C02-C11 in the third embodiment. The description thereof is left out.

In step D03, the control part 10 determines if there is record instructing operation. The first embodiment is taken for example. When the display part 4 displays the display interface 1705 in FIG. 17, the user presses the record key of the operation part 11 to perform the next step. However, the invention is not limited thereto. Even if there is no specified record instructing operation, the control part 10 may automatically perform step D04, based on the specified record condition. For example, the specified record condition may be that the control part 10 determines the specified time interval, the temperature value in the thermal image exceeds the specified threshold, or triggering signals of other sensors connected with the thermal imaging device 13 are detected.

In step D04, record processing is performed.

The control part 10 as a record part records the specified infrared data with the specified record information, in response to the record instructing operation or according to the specified record condition. Then, perform step D05.

The infrared data is the thermal imaging data acquired by the photographing part (the acquiring part) and/or the data acquired after specified processing for the thermal imaging data acquired by the photographing part. The specified infrared data may be the thermal imaging data (frame) acquired according to signals read by the infrared detector in response to the record instructing operation or at the moment (or the later specified moment) that the specified record condition is satisfied, the specified thermal imaging data (frame) in the multiple frames of the thermal imaging data stored in the temporary storage part 6 in response to the record instructing operation or at the moment (or the later specified moment) that the specified record condition is satisfied, the data acquired after specified processing (the specified processing may be modification, interpolation, pseudo-color, temperature value conversion, pixel reduction, compression, or a combination thereof) for the above thermal imaging data, the record specified number of the multi-frame thermal imaging data, the thermal imaging data (frame) acquired after specified processing for the specified number of the multi-frame thermal imaging data, such as one-frame thermal imaging data acquired after integral calculation for the multi-frame thermal imaging data stored in the temporary storage part 6, or a combination thereof. For example, the infrared data may include the temperature value of each pixel acquired by the thermal imaging data and the image data of the infrared thermal image.

The specified record information as shown in FIG. 29 may one or a combination of the followings:

1) the selected body information (the specified part or all of the body information);

2) the constituted data (or identity information of the constituted data such as a file name) of the designated reference image and/or the position information of the reference image in the infrared thermal image;

3) the constituted data (or the identity information of the constituted data such as a file name) of the designated analysis area and/or the position information of the analysis area in the infrared thermal image;

4) other constituted data (or the identity information of the constituted data such as a file name) having the specified position relation with the reference image or the analysis area and/or the position parameter of the object acquired by the other constituted data in the infrared thermal image, such as, the constituted data acquired by computing and/or processing a designated object and/or the position information of the object acquired by the constituted data in the infrared thermal image;

5) the analysis mode to which the analysis area corresponds;

6) the analysis result;

7) the diagnosis rule to which the analysis mode corresponds;

8) the diagnosis result.

When the configuration is as shown in FIG. 13, the corresponding position information is acquired according to the position rule in FIG. 13, and when the configuration is as shown in FIG. 14, the corresponding position information is acquired according to the position rule in FIG. 14. Obviously, when the position parameter of the analysis area is adjusted, the position information to be record may be the position parameter after adjustment.

One embodiment of the relevance record is that the specified record information is as the information attachment of the infrared data with a specified format. In detail, in one embodiment (the first embodiment), in response to the record instructing operation of the operation part 11, the control part 10 controls the infrared detector to read signals to acquire the thermal imaging data, allows the image processing part 2 to perform specified compression for the thermal imaging data or to perform compression after the specified processing such as modification or interpolation for the thermal imaging data, then determines if the temporary storage part stores the specified record information at the specified area, if yes, allowing the specified record information stored at the specified area of the temporary storage part 6 to be related with the compressed thermal imaging data, thus to generate a thermal image file record to the storage card 8, and finally finishes the processing. In addition, the compression may be performed after the specified record information is attached. If no, the thermal image file generated by the compressed thermal imaging data is record to the storage card 8. The record storage medium is not limited to the storage card 8 or the flash memory 9, and may be a network destination communicated via the communication I/F 5.

FIG. 31 is a schematic diagram showing a structure of a thermal image file. The infrared data 3101 is the thermal imaging data acquired by reading from the infrared detector in response to the record instructing operation or according to the specified record condition. According to the configuration in FIG. 29, the information included by the specified record information 3102 is the photographed body 1, the constituted data of T1, the constituted data of F1, the position information of the contour image T1, the position information of the analysis area F1, the analysis mode 1, and the analysis and diagnosis result (the specified analysis and diagnosis result in response to the record instruction, the analysis and diagnosis result at that moment or the specified analysis and diagnosis result after pressing the analysis key in the first embodiment, such as the analysis and diagnosis result of the maximum temperature difference). Other attachment information 3103 may be photographing time.

FIG. 32 is a schematic diagram showing an infrared thermal image IR0 to which the thermal imaging data record when visually matched with the reference image T1 corresponds. The position and dimension of the thermal image IR1 of the photographed body in the infrared thermal image IR0 are standard. The position information of T1 represents the position parameter of IR1 in the infrared thermal image IR0, and the "position information of F1" represents the position parameter of F1 in the infrared thermal image IR0.

In addition, during the relevance record processing, the specified record information may be record to an information file or an index file related to the thermal image file, and the control part 10 may generate the information file or the index file. In addition, a file name of the thermal image file may be generated according to the body information or the identity information of the constituted data. The essence of the relevance record is to record the information that is convenient for the subsequent batch processing analysis. For example, the record of the body information is convenient for classifying the infrared data subsequently, the record of the constituted data and the position information of the reference image is convenient for subsequently setting the analysis area for being analyzed by batch processing, the record of the constituted data and the position information of the analysis area is convenient for subsequent fast batch processing analysis, and the record of the analysis result and the diagnosis result may reduce the processing time and load of the subsequent batch processing.

In step D05, determines if the diagnosis mode is exited. If no, return to the step D02, repeat the above steps, and the user can record for multiple times. If yes, end.

According to the above, since the reference image and the analysis area are used for assisting the photographing of the thermal image of the photographed body, the photographing quality is improved, and the subsequent analysis and diagnosis batch processing is facilitated by relating and recording the specified record information related to the analysis and diagnosis.

Embodiment Five

In this embodiment, in a thermal imaging device with the same structure of the thermal imaging device 13 in FIG. 1, the flash memory 9 stores the control programs of setting the reference image and the analysis area, adjusting the reference image and analysis area, analyzing and diagnosing, for the replayed infrared thermal image in a replay mode.

For example, in the replay mode, the infrared data (such as the thermal imaging data acquired by selecting the thermal image file to be processed from the storage card 8) to be processed is selected. First, if the infrared data (frame) includes the information related to the analysis area and reference image, such as the constituted data related and stored with the infrared data, the position parameter of the reference image or analysis area, the identity information of the constituted data, or the body information, is determined. If yes, the analysis area is determined according to the related information, and then according to the specified analysis mode and diagnosis rule, the infrared data is analyzed and diagnosed to acquire the analysis and diagnosis result. Otherwise, the reference image reflecting the morphological character of the photographed body may be displayed with the infrared thermal image acquired by the infrared data to be processed together, and the user can observe the visual matching degree of the reference image and the thermal image of the photographed body. If no, the file name, the number, or the thumbnail related to the identity indicator of the constituted data are provided for the users to select. Then, the reference image reflecting the morphological character of the photographed body is displayed with the infrared thermal image acquired by the infrared data to be processed. If the thermal image of the photographed body matches the reference image in visual, the analysis area having the specified position relation with the reference image and the corresponding analysis mode and diagnosis rule may be allocated for analysis. If the matching degree is not great, the user may adjust the position, dimension, or rotating angle of the reference image to match the thermal image of the photographed body in the infrared thermal image. When matched in visual, the analysis area having the specified position relation with the reference image is determined, and the analysis and diagnosis is performed according to the specified analysis mode and the diagnosis rule.

This invention is not limited to the thermal imaging device with the photographing function. In the embodiment, a thermal image processing device (such as a computer, a personal digital assistant, a display device used in a set with the thermal imaging device with the photographing function) is as an example of a device for diagnosing thermal images, for arranging the infrared data (such as the thermal image file).

Embodiment Six

The thermal imaging data in the invention is not necessary to be acquired via photographing. The invention may also be applied to a thermal image processing device receiving and processing the thermal imaging data (thermal image transferring data) from an external part. The thermal image transferring data may be the thermal imaging data (the AD value), the infrared thermal image generated by the thermal imaging data, the compressed thermal imaging data, or the data acquired by compressing the infrared thermal image. In the sixth embodiment, a thermal image processing device 100 is as an example of the device for diagnosing thermal images.

Figure 33:
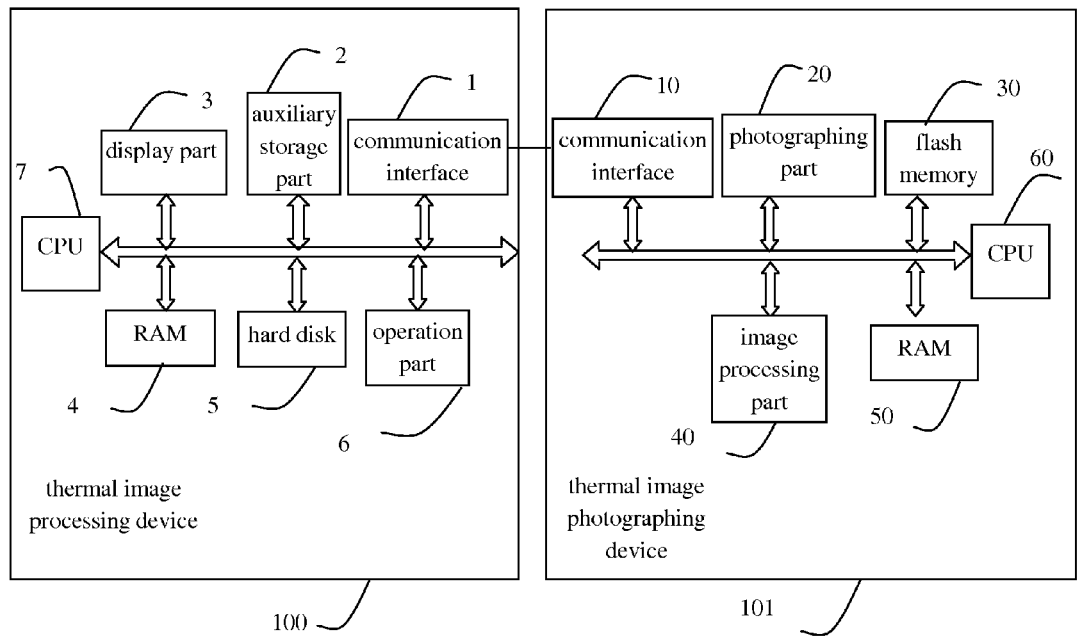
FIG. 33 is a block diagram showing a thermal image diagnosing system including a thermal image processing device 100 and a thermal image photographing device 101 connected with each other according to a sixth embodiment.

FIG. 33 is a block diagram showing a thermal image processing system including a thermal image processing device 100 and a thermal image photographing device 101 connected with each other.

The thermal image processing device 100 includes a communication interface 1, an auxiliary storage part 2, a display part 3, a RAM 4, a hard disk 5, an operation part 6, and a CPU 7 for the overall control connected with the above parts via a bus. The thermal image processing device 100 may be a personal computer, a personal digital assistant, or a display part used in a set with the thermal image photographing device. Based on the control of CPU 7, the thermal image processing device 100 receives the thermal image transferring data output from the thermal image photographing device 101 connected with the thermal image processing device 100 via the communication interface 1.

The communication interface 1 is used for continuously receiving the thermal image transferring data output from the thermal image photographing device 101, such as the thermal image transferring data transferred via a relay device (the thermal image transferring data output from the thermal image photographing device 101 is transferred via the relay device), and may be as the communication interface for controlling the thermal image photographing device 101. In the embodiment, the communication interface 1 includes different kinds of wired or wireless communication interfaces, such as a network interface, a USB interface, a 1394 interface, or a video interface, on the thermal image processing device 100.

The auxiliary storage part 2 may be the storage medium such as a CD-ROM or a storage card and the related interface.

The display part 3 may be a liquid display or may be other displays connected with the thermal image processing device 100, while the thermal image processing device 100 does not include the display in itself.

The RAM 4 is as a buffer storage for temporarily storing the thermal image transferring data received via the communication interface 1 and is as a working storage of the CPU 7 for temporarily storing the data processed by the CPU 7.

The hard disk 5 stores control programs and different data used in the control.

The structure of the thermal imaging device 13 removing the photographing part 1 is similar to the thermal image processing device 100. The thermal image transferring data that is acquired is also suitable for the embodiment. Therefore, the description of the embodiment is left out.

The CPU 7 performs the function of the image processing part and is used for performing specified processing for the received thermal image transferring data to acquire the image data of the infrared thermal image. The specified processing may be conversion processing to acquire data suitable for displaying and recording, such as modification, interpolation, pseudo-color, synthesis, compression, or decompression. The CPU 7 performs different processing according to different formats of the thermal image transferring data. In one embodiment, when the received thermal image transferring data is the compressed thermal imaging data, the specified processing may be that the CPU 7 decompresses the thermal image transferring data received by the acquiring part and performs the corresponding specified processing. In one embodiment, the specified processing after decompressing the compressed thermal imaging data (the thermal image transferring data) may be pseudo-color processing, to acquire the image data of the infrared thermal image. In addition, the specified processing may be specified different processing such as modification or interpolation for the decompressed thermal image transferring data. In another embodiment, for example, when the received thermal image transferring data is the image data of the compressed infrared thermal image, the image data of the infrared thermal image is acquired via decompression. In another embodiment, for example, when the communication interface 1 receives the analog infrared thermal image, the image data of the digital infrared thermal image after AD conversion of related AD conversion circuits is transferred to the temporary storage part 6.

The thermal image photographing device 101 may be a thermal image photographing device of different types, and is used for photographing the photographed body and outputting the thermal image transferring data. In FIG. 33, the thermal image photographing device 101 includes a communication 10, a photographing part 20, a flash memory 30, an image processing part 40, a RAM 50, and a CPU 60. The CPU 60 controls the whole action of the thermal image photographing device 101, and the flash memory 30 stores control programs and different data used in each control. The photographing part 20 includes an optical part, a driving part, a thermal image sensor, and a signal preprocessing circuit, for photographing to acquire the thermal imaging data. The thermal imaging data is temporarily stored in the RAM 50, and then is processed (such as compression) by the image processing part 40 (such as a DSP) to acquire the thermal image transferring data that is output via the communication interface 10. According to difference of design and using aims, for example, the thermal imaging data output by the thermal image photographing device 101 may be the thermal imaging data after specified processing, the image data of the thermal image (the image data of the thermal image generated by the thermal imaging data), the data after compression by a specified format for the thermal imaging data or the image data of the thermal image, or a combination thereof, which is generally called as thermal image transferring data. In the embodiment, the thermal image photographing device 101 is used for photographing and outputting the thermal image transferring data, and has the function similar to the photographing part 1 of the thermal imaging device 13.

Figure 34:
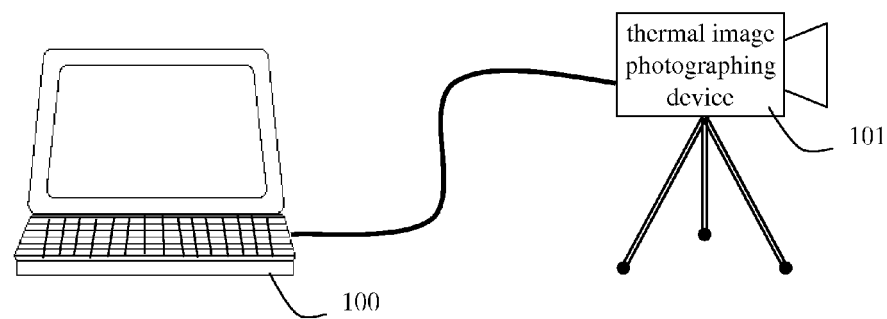
FIG. 34 is a schematic diagram showing a thermal image diagnosing system including the thermal image processing device 100 and the thermal image photographing device 101 connected with each other.

FIG. 34 is a schematic diagram showing the thermal image processing system including the thermal image processing device 100 and the thermal image photographing device 101 connected with each other.

The thermal image photographing device 101 is erected on a detecting vehicle via a cloud ladder and is connected with the thermal image processing device 100 via a special-use cable such as a communication wire or a wired or wireless local area network. The users may watch and monitor the thermal image of the photographed body via the thermal image processing device 100. The thermal image photographing device 101 is connected with the thermal image processing device 100 to form an information recording system in the embodiment, for photographing the photographed body to acquire the thermal imaging AD data and outputting the thermal image transferring data.

To sum up, preferably, the constituted data of the reference image has the specified position relation with the constituted data of the analysis area, and the displayed reference image and the analysis area related to analysis satisfy the specified position relation. The reference image designating part and the analysis area determining part determine the constituted data of the reference image and the analysis area according to the constituted data with the specified position relation. For example, the constituted data therebetween may be determined from the constituted data with the specified position relation prestored in the storage medium. For example, the constituted data of the analysis area may be determined from the constituted data acquired by processing and/or computing a designated object such as the constitute data of the reference image, and the specified position relation between the constituted data acquired by computing and/or processing and the designated object may be determined via the corresponding computing rule or processing rule. In addition, the specified position relation of the constituted data may be defined by the position rule (such as the position parameter is set according to the original dimension and centering of the object acquired by the constituted data) defaulted by the thermal imaging device 13.

Further, the constituted data with the specified position relation may be configured temporarily. For example, the constituted data of the analysis area may be configured according to the specified position relation between the reference image and the analysis area. For example, the analysis area may be set according to the position parameter of the reference image in the infrared thermal image, based on the specified position in the reference image. The specified position may be a coordinate position. The coordinate position may be prestored and related with the constituted data of the reference image, or may be acquired by computing and/or processing the constituted data of the reference image. The analysis area may be set according to the constituted data (such as points, lines, or planes) of the analysis area temporarily configured according to the coordinate position. Therefore, the analysis area may be the analysis area that is set based on the specified position having the specified position relation with the reference image.

Further, when the storage medium is used for storing the constituted data of the reference image, the constituted data of the related analysis area, and the position information of the reference image and the analysis area in the infrared thermal image, the reference image position setting part and the analysis area position setting part are used for setting the respective position parameter of the reference image and the analysis area in the infrared thermal image according to the position information of the reference image and the analysis area in the infrared thermal image.

In addition, the constituted data of the reference image and the analysis area may be determined from the constituted data without the specified position relation. For example, if the specified position relation between the constituted data of the reference image and the constituted data of the analysis area selected from the constituted data related to the constituted data of the reference image or the constituted data related to the same body information may not be prestored, the user may set the position parameter therebetween. Since there is the reference of the reference image, the invention is more convenient than the prior art.

In the invention, the program record on the storage part may be executed to perform the computer (such as a CPU or a MPU) of the system or equipment with the function in the above embodiment, and the computer of the system or equipment may read and execute the program record on the storage part to perform the function in the above embodiment. To achieve the objective, the program acquired from the network or the record medium (such as a computer readable medium) as the storage device is provided for the computer.

Although the function block in the figures may be realized via hardware, software, or a combination thereof, the function block may be not necessary to be realized in one-by-one mode. For example, one software or hardware unit may be used for realizing multiple function blocks, or multiple software or hardware units may be used for realizing one function block. In addition, the processing and control functions of parts or whole in the embodiments may be realized via a special-use circuit, a general processor, or a programmable FPGA.

Preferably, the phonic way may be used for informing. Correspondingly, the data of the sound library may be stored (such as the sound corresponding to the analysis and diagnosis result, or the sound generated by the sound data corresponding to characters according to the content of the analysis and diagnosis result).

Although multiple embodiments of the constituted data of the reference image and the analysis area, position setting of the reference image and the analysis area, determination of the analysis mode and the diagnosis rule, the setting of the synthesis parameter, and the switch setting are described, the users may configure the above processing. However, the invention is not limited thereto. For example, when the thermal imaging device 13 leaves the factory, one or a combination of the above settings may be configured. When the specified designated type of the constituted data of the reference image and the analysis area, the position rule of the reference image and the analysis area, the synthesis parameter, the analysis mode, and the diagnosis rule are configured before leaving the factor, the settings may be performed for the constituted data in the storage medium according to the configuration dispatched from the factory. Otherwise, part items are configured before leaving the factory, and users configure other parts. In the embodiment, the above advantages may be achieved by a series of represented embodiments, and any product performing the embodiment of the invention is not necessary to achieve all of the advantages at the same time.

In addition, in the embodiment, the electric power industry as the scene is taken for example, and different fields of the infrared detection are also applied.

The above description is just detailed embodiments of the invention, and different examples and description does not limit the substantive contents of the invention. After reading the description, persons having ordinary skill in the art may make various modifications and changes without departing from the scope and spirit of the invention.

What is claimed is:

1. A device for diagnosing thermal images, comprising:
    an acquiring part for acquiring thermal imaging data;
    a body information selecting part for selecting body information from the body information stored in a storage medium, the storage medium being used for storing the body information and the constituted data related to the body information; the body information being composed of attribute information of multiple attributes, and the body information being finally selected via display and multiple selections for the attribute information of multiple attributes of the body information;
    a display controlling part for controlling to display a reference image acquired according to designated constituted data and an infrared thermal image generated by the acquired thermal imaging data together according to a position parameter of the reference image located in the infrared thermal image, the reference image reflecting morphological characters of a photographed body;
    a thermal image analyzing part for analyzing the thermal imaging data acquired by the acquiring part to acquire an analysis result, according to a specified analysis mode, based on a specified analysis area;

a diagnosing part for diagnosing according to a specified diagnosis rule to acquire a diagnosis result according to the analysis result acquired by the thermal image analyzing part;

wherein the analysis area is acquired by the constituted data satisfying a specified position relation with the constituted data of the reference image, and the displayed reference image and the analysis area satisfy the specified position relation; and when the reference image performs a dimension scaling, the analysis area performs a same dimension scaling based on a same base point, to remain a same dimension scale.

2. The device for diagnosing thermal images according to claim 1, wherein the analysis mode at least comprises an analysis mode related to the analysis area.

3. The device for diagnosing thermal images according to claim 2, wherein the analysis mode at least comprises one or a combination of the followings:
   1) the analysis mode acquired according to analysis mode information related to the constituted data of the analysis area;
   2) the analysis mode acquired according to the analysis mode information related to a position rule or position information related to the position parameter of the analysis area;
   3) the analysis mode acquired according to the analysis mode information related to corresponding computing and/or processing rule and/or the analysis mode information related to a designated object, when the constituted data of the analysis area is acquired by computing and/or processing the designated object.

4. The device for diagnosing thermal images according to claim 2, wherein the diagnosis rule at least comprises a diagnosis rule set according to the diagnosis rule related to the analysis mode which is related to the analysis area.

5. The device for diagnosing thermal images according to claim 1, wherein the analysis mode at least comprises an analysis mode related to the analysis area, and the diagnosis rule at least comprises a diagnosis rule set according to the diagnosis rule related to the analysis mode.

6. The device for diagnosing thermal images according to claim 1, further comprising:
   the reference image being acquired according to the constituted data related to the selected body information.

7. The device for diagnosing thermal images according to claim 6, wherein the analysis area is acquired by the constituted data satisfying a specified position relation with the constituted data of the reference image, and the displayed reference image and the analysis area satisfy the specified position relation.

8. The device for diagnosing thermal images according to claim 6, wherein the storage medium is used for storing the body information and the constituted data with a specified position relation related with the body information;
   the reference image and the analysis area are acquired according to the constituted data with the specified position relation related to the selected body information.

9. The device for diagnosing thermal images according to claim 6, wherein the storage medium is used for storing the body information, the constituted data related to the body information, the analysis mode information related to the constituted data, and the diagnosis rule information related to the analysis mode information;

the analysis area is acquired according to the constituted data related to the selected body information;

the analysis mode at least includes the analysis mode acquired by the analysis mode information related to the constituted data for acquiring the analysis area;

the diagnosis rule at least includes the diagnosis rule acquired according to the diagnosis rule information related to the analysis mode information.

10. The device for diagnosing thermal images according to claim 1, wherein the constituted data related to the analysis area at least comprises the constituted data acquired by processing a designated object according to a specified processing rule and/or computing the designated object according to a specified computing rule.

11. The device for diagnosing thermal images according to claim 1, wherein the analysis area is an analysis area set according to a specified position satisfying the specified position relation with the reference image.

12. The device for diagnosing thermal images according to claim 1, wherein the position parameters of the reference image and the analysis area are set according to at least one of the followings:
   1) the position parameter of the analysis area is set according to the position parameter of the reference image in the infrared thermal image and a specified position relation between the reference image and the analysis area;
   2) the position parameter of the reference image is set according to the position parameter of the analysis area in the thermal imaging data and the specified position relation between the reference image and the analysis area;
   3) the position parameter of the reference image and/or the analysis area is set according to the specified position relation between the reference image and/or the analysis area and a main object and the position parameter of the main object in the infrared thermal image;
   4) according to position information related to the constituted data, the position parameter of the reference image acquired by the constituted data in the infrared thermal image is set, and the position information represents the position information of the reference image acquired by the constituted data in the infrared thermal image,
   according to position information related to the constituted data, the position parameter of the analysis area acquired by the constituted data in the thermal imaging data is set, and the position information represents the position information of the analysis area acquired by the constituted data in the thermal imaging data.

13. The device for diagnosing thermal images according to claim 1, further comprising:
   the storage medium for storing at least one body information, related multiple constituted data with a specified position relation, analysis mode information related to the constituted data capable of acquiring the analysis area, and diagnosis rule information related to the analysis mode information;
   the reference image being acquired according to the constituted data related to the selected body information;
   the constituted data related to the analysis area being determined according to the constituted data related to the selected body information;

the analysis mode at least including the analysis mode acquired according to the analysis mode information related to the constituted data for acquiring the analysis area;

the diagnosis rule at least including the diagnosis rule acquired according to the diagnosis rule information related to the analysis mode information.

14. The device for diagnosing thermal images according to claim 1, further comprising an informing control part for controlling to inform the diagnosis result.

15. The device for diagnosing thermal images according to claim 1, further comprising an informing control part for controlling to display the diagnosis result, the diagnosis result including one or a combination of a diagnosis result, a diagnosis threshold related to the diagnosis, a diagnosis basis, a defect type, a defect extent, and a processing proposal.

16. The device for diagnosing thermal images according to claim 1, further comprising a configuration part for configuring a specified designated type of the constituted data of the reference image, a specified designated type of the constituted data of the analysis area, the specified position relation between the reference image and the analysis area, a position setting rule of the reference image and the analysis area, a synthesis parameter, the analysis mode to which the analysis area corresponds, the diagnosis rule to which the analysis mode corresponds, or a combination thereof.

17. The device for diagnosing thermal images according to claim 1, wherein the device for diagnosing thermal images is a portable thermal imager, and the acquiring part is a photographing part for continuously photographing and acquiring the thermal imaging data.

18. The device for diagnosing thermal images according to claim 1, further comprising a record part for recording specified record information with the acquired thermal imaging data or the data acquired after specified processing for the acquired thermal imaging data, the specified record information at least comprising information of the diagnosis result or the information of the analysis result and the diagnosis result.

19. A method for diagnosing thermal images, comprising:
an acquiring step for acquiring thermal imaging data;
a body information selecting step for selecting body information from the body information stored in a storage medium, the storage medium being used for storing the body information and the constituted data related to the body information; the body information being composed of attribute information of multiple attributes, and the body information being finally selected via display and multiple selections for the attribute information of multiple attributes of the body information;
a display controlling step for controlling to display a reference image acquired according to designated constituted data and an infrared thermal image generated by the acquired thermal imaging data together according to a position parameter of the reference image located in the infrared thermal image, the reference image reflecting specified morphological characters of a photographed body;
a thermal image analyzing step for analyzing the thermal imaging data acquired in the acquiring step to acquire an analysis result, according to a specified analysis mode, based on a specified analysis area;
a diagnosing step for diagnosing according to a specified diagnosis rule to acquire a diagnosis result according to the analysis result acquired in the thermal image analyzing step;
wherein the analysis area is acquired by the constituted data satisfying a specified position relation with the constituted data of the reference image, and the displayed reference image and the analysis area satisfy the specified position relation; and
when the reference image performs a dimension scaling, the analysis area performs a same dimension scaling based on a same base point, to remain a same dimension scale.

20. The method for diagnosing thermal images according to claim 19, wherein the analysis mode at least comprises an analysis mode related to the analysis area, and the diagnosis rule at least comprises a diagnosis rule set according to the diagnosis rule related to the analysis mode which is related to the analysis area.

21. The method for diagnosing thermal images according to claim 19, wherein the analysis area is an analysis area set according to a specified position satisfying the specified position relation with the reference image.

22. The method for diagnosing thermal images according to claim 19, comprising:
the reference image being acquired according to the constituted data related to the selected body information.

23. The method for diagnosing thermal images according to claim 22, comprising:
a storage medium for storing the body information, the related multiple constituted data satisfying the specified position relation, the analysis mode information related to the constituted data capable of acquiring the analysis area, and the diagnosis rule information related to the analysis mode information;
the body information selecting step for selecting the body information;
the reference image being acquired according to constituted data related to the selected body information;
the constituted data related to the analysis area being determined according to the constituted data related to the selected body information;
the displayed reference image and the analysis area satisfying the specified position relation between the constituted data of the reference image and the constituted data of the analysis area;
the analysis mode at least including an analysis mode acquired according to the analysis mode information related to the constituted data for acquiring the analysis area;
the diagnosis rule at least including a diagnosis rule acquired according to the diagnosis rule information related to the analysis mode information.

24. The method for diagnosing thermal images according to claim 19, further comprising:
an informing control step for controlling to display the diagnosis result, the diagnosis result including one or a combination of a diagnosis result, a diagnosis threshold related to the diagnosis, a diagnosis basis, a defect type, a defect extent, and a processing proposal.

* * * * *